US008728748B2

(12) United States Patent
Gougeon et al.

(10) Patent No.: US 8,728,748 B2
(45) Date of Patent: May 20, 2014

(54) HMGB1 AND ANTI-HMGB1 ANTIBODIES FOR THE PROGNOSTIC OF NEUROLOGICAL DISORDERS

(75) Inventors: Marie-Lise Gougeon, Clamart (FR); Beatrice Poirier-Beaudoin, Beynes (FR); Valerie Seffer, Brunoy (FR); Hela Saidi, Villejuif (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 13/583,031

(22) PCT Filed: Mar. 10, 2011

(86) PCT No.: PCT/EP2011/053656
§ 371 (c)(1),
(2), (4) Date: Nov. 19, 2012

(87) PCT Pub. No.: WO2011/110650
PCT Pub. Date: Sep. 15, 2011

(65) Prior Publication Data
US 2013/0065221 A1 Mar. 14, 2013

(30) Foreign Application Priority Data
Mar. 10, 2010 (EP) ................................... 10290124

(51) Int. Cl.
G01N 33/53 (2006.01)
G01N 33/536 (2006.01)
G01N 33/537 (2006.01)
G01N 33/564 (2006.01)

(52) U.S. Cl.
USPC ......... 435/7.92; 435/7.1; 435/7.9; 424/184.1; 600/410; 436/506; 436/507

(58) Field of Classification Search
None
See application file for complete search history.

(56) References Cited

PUBLICATIONS

Urbonaviciute et al. Factors masking HMGB1 in human serum and plasma. Journal of Leukocyte Biology, Jan. 2007, vol. 81, p. 67-74.*
Bustin et al. Antigenic Determinants of High Mobility Group Chromosomal Proteins 1 and 2. Biochemistry 1982, vol. 21, pp. 6773-6777.*
Wisniewski et al. Region of Insect High Mobility Group (HMG) 1 Protein Homologous to Helix 2 of the Rat HMG1-B Box is in Close Contact with DNA. The Journal of Biological Chemistry 1994, vol. 269, No. 46, pp. 29261-29264.*
Nowak et al. Elevated Plasma Levels of High Mobility Group Box protein 1 in Patients with HIV-1 Infection. AIDS 2007, vol. 21, No. 7, pp. 869-871.*
Thierry et al. High-mobilitygroup box 1 protein induces HIV-1 expression from persistently infected cells. AIDS 2007, vol. 21, pp. 283-292.*
Yamada et al. High Mobility Group Protein 1 (HMGB1) Quantified by ELISA with a Monoclonal Antibody That Does Not Cross-React with HMGB2. Clinical Chemistry 2003, vol. 49, No. 9, pp. 1535-1537.*
Okamoto et al. IP-10/MCP-1 ratio in CSF is a useful diagnostic marker of neuropsychiatric lupus patients. Rheumatology 2006, vol. 45, pp. 232-234.*

* cited by examiner

*Primary Examiner* — Louise Humphrey
(74) *Attorney, Agent, or Firm* — Law Office of Salvatore Arrigo and Scott Lee, LLP

(57) ABSTRACT

The invention relates to in vitro method for quantitating the antibodies specific for High mobility group box I (HMGB1) contained in a sample, in particular a serum sample or a cerebrospinal fluid sample obtained from a patient, and the use of this method in the prognostic and/or diagnosis of neurological disorders. These methods are in particular applicable to the monitoring of the human immunodeficiency virus (HIV) infection of a subject who is known to be infected with HIV and in the prognostic and/or diagnostic of the state of progression of Acquired immune deficiency syndrome (AIDS) or the state of progression toward AIDS, in particular the state of progression or the state of progression toward neurological disorders associated with AIDS. Finally, the invention is also about method to determine the immune deficiency or level of immune activation of a patient, in particular a HIV-infected patient.

25 Claims, 27 Drawing Sheets

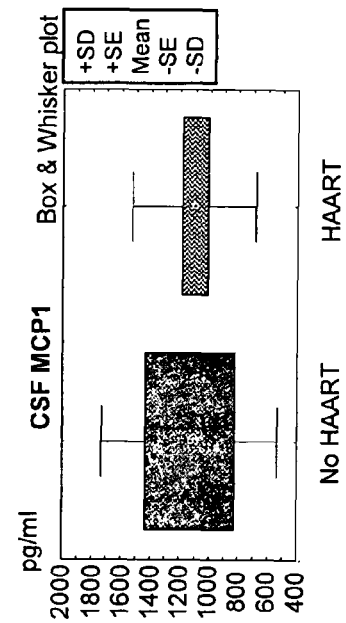
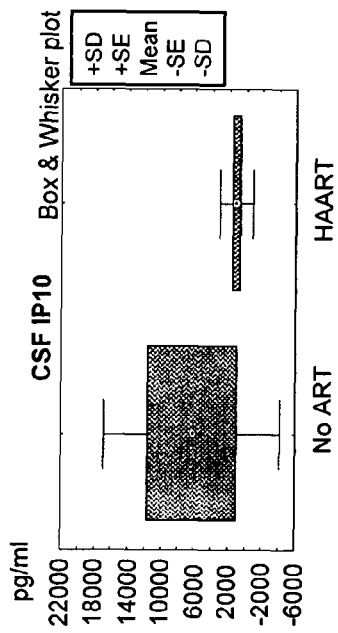
C
Fig. 10

| | All patients median (IQR) | No HAND median (IQR) | HAND median (IQR) | p-value HAND vs no HAND |
|---|---|---|---|---|
| Number of patients | 103 | 73 | 30 | / |
| HIV RNA ($log_{10}$ copies/ml) at inclusion | 1.6 (1.6-2.41) | 1.6 (1.6-2.62) | 1.6 (1.6-2.08) | NS |
| CD4 count (cells/mm$^3$) | 495 (357-741) | 480 (372-729) | 499 (351-754) | NS |
| Nadir CD4 count (cells/mm$^3$) | 216 (75-350) | 216 (78-372) | 207 (58-340) | NS |
| On anti-retroviral therapy (n, %) | 86 (81%) | 59 (81%) | 24 (80%) | NS |
| Viremic (n, %) | 34 (33%) | 23 (31%) | 11 (36%) | NS |
| % T CD8$^+$CD38$^+$HLA-DR$^+$ | 13.4 (7.1-25.2) | 13.6 (7-25.6) | 13.4 (7.7-24.3) | NS |
| % T CD4$^+$CD38$^+$HLA-DR$^+$ | 4.2 (2.8-8.4) | 3.75 (2.7-8.4) | 4.9 (3.2-7.7) | NS |
| Circulating HMGB1 (ng/ml) | 6.29 (3.4-10.8) | 7.4 (5.2-11.6) | 3 (1.6-10) | 0.006 |
| Total anti-HMGB1 (ng/ml) | 1188 (848-1855) | 1166 (808-1696) | 1285 (1047-2134) | 0.05 |
| IP10 (pg/ml) | 953 (405-1533) | 969 (375-1666) | 832 (534-1359) | NS |
| MCP1 (pg/ml) | 267 (195-400) | 261 (198-374) | 292 (179-462) | NS |

Fig. 14

HMGB1 AND ANTI-HMGB1 ANTIBODIES FOR THE PROGNOSTIC OF NEUROLOGICAL DISORDERS

This application is the U.S. National Stage of International Application PCT/EP2011/053656, filed Mar. 10, 2011, which claims the benefit of European Application 10290124.6, filed Mar. 10, 2010. All of these applications are incorporated herein by reference.

BACKGROUND OF THE INVENTION

1. Field of the Invention

The application relates to the quantitation of the protein HMGB1 or of the antibodies specific for HMGB1 in biological sample, in particular serum and CerebroSpinal Fluid (CSF), and their respective correlation with prognostic methods of the state of progression of neurological disorders or toward neurological disorders, in particular neurological disorders associated with HIV infection and with diagnostic methods. The invention also relates to the correlation of the protein HMGB1 or of the antibodies specific for HMGB1 with the monitoring of HIV infection or with viral load as well as prognostic methods of the state of progression of AIDS.

2. Description of the Related Art

Shortly after infection, HIV-1 is able to penetrate the brain, eventually resulting in HIV-1 associated complications in the Central Nervous System (CNS). HIV associated dementia (HAD) is clinically characterized by motor and behavioral dysfunctions leading to seizures, coma, and death within 6 months of onset. HIV-encephalitis, the pathological correlate of HAD, is characterized by widespread astrogliosis, oxidative stress, cytokine/chemokine dysregulation, and neuronal degeneration (Gonzalez-Scarano and Martin-Garcia, Nat Rev Immunol 2005, 5: 69-81). Since neurons are not infected by HIV-1, the current thinking is that these cells are damaged indirectly by pro-inflammatory chemokines released by activated glial cells. IP-10 (CXCL10) is a neurotoxic chemokine that is upregulated in astroglia and has been suggested to enhance retrovirus infection and mediate neuronal injury. Elevation of IP-10 in CSF was reported in HIV-infection, and its level correlated with CSF HIV viral load (Cinque P et al. J Neuroimmunol 2005, 168:154). It was also reported a possible association between CSF macrophage chemoattractant protein 1 (MCP-1 or CCL2) levels and the development of HAD in a HAART-experienced cohort with advanced HIV infection (Sevigny J J, Albert S M, McDermott M P; et al. Neurology. 2004;63:2084). Another study reported an association between plasma MCP-1 levels and HIV-associated dementia (Sevigny et al. Arch. Neurol. 2007, 64:97).

The high mobility group box 1 (HMGB1) protein is a non-histone chromosomal protein that acts as a potent proinflammatory cytokine when actively secreted from activated macrophages, monocytes, dendritic cells or other cells such as NK cells. HMGB1 behaves as a trigger of inflammation, attracting inflammatory cells, and of tissue repair, recruiting stem cells and promoting their proliferation. Moreover, HMGB1 activates dendritic cells (DCs) and promotes their functional maturation and their response to lymph node chemokines. Activated leukocytes actively secrete HMGB1 in the microenvironment. Thus, HMGB1 acts in an autocrine/paracrine fashion and sustains long-term repair and defense programs (Bianchi and Manfredi, 2007; Lotze and Tracey, 2005).

In recent studies, HMGB1 was shown to trigger HIV-replication in HIV-infected DC, thus contributing to the constitution of viral reservoirs in DCs (Saidi H, Melki M-T, Gougeon M-L, PLoS One 2008). Considering that DCs are the first targets for HIV in the first hours of mucosal infection, which will then migrate to secondary lymphoid organs where they will transmit HIV to T cells, these findings challenge the question of the in vivo involvement of HMGB1 in the triggering of viral replication and replenishment of viral reservoirs. HMGB1 was produced during a cross-talk between HIV-infected DCs and activated NK cells, also resulting in resistance of HIV-infected DCs to NK killing. DC survival was associated with the upregulation of two apoptosis inhibitors, c-IAP2 and c-FLIP in infected DCs, a process induced by HMGB1 (Melki M-T et al. PLoS Pathogens 2010, 6 (4) e1000862). Blocking HMGB1 activity by specific inhibitors, such as glycyrrhizin or blocking antibodies, abrogates HIV replication in infected DCs (Saidi H, Melki M-T, Gougeon M-L, PLoS One 2008), and restores the susceptibility of infected DCs to NK killing (Melki M-T et al. PLoS Pathogens 2010, 6(4) e1000862). These findings, which provide new insights into how HIV hijacks DCs to promote viral dissemination and to maintain viability of long-term reservoirs, have made the object of patent application PCT/EP2009/06828.

These findings also challenge the question of the in vivo involvement of HMGB1 in the triggering of viral replication and replenishment of viral reservoirs. To address this question, HMGB1 concentration in sera from HIV-infected patients have been quantified (Elisa, Shino test, IBL) to assess the in vivo contribution of circulating HMGB1 to plasma HIV viral load and to disease evolution. Moreover, considering that auto-antibodies specific for HMGB1 could be found in autoimmune diseases such as SLE (lupus) (Hayashi et al., 2009), a specific Elisa assay was developed to check whether anti-HMGB1-specific antibodies in sera from HIV-infected patients were detected in HIV disease.

The measure of both HMGB1 and anti-HMGB1 antibodies in patients' sera has been reported in patent application PCT/EP2009/06828. The following conclusions have been drawn up:

(i) chronic HIV infection triggers the production of HMGB1, detected at increased levels in sera from infected patients, which in turn induces the production of neutralizing antibodies;

(ii) an inverse correlation is detected between HMGB1 and anti-HMGB1 antibodies (Abs), indicating that when HMGB1 is bound to the antibodies, it is not detected anymore in serum samples;

(iii) the more anti-HMGB1 antibodies (meaning the more HMGB1 produced earlier) in sera, the less CD4 T cells, suggesting that increased levels of serum anti-HMGB1 antibodies are associated with disease evolution; and (iv) potent anti-retroviral therapy (HAART) reduces serum levels of both HMGB1 and anti-HMGB1 antibodies and may normalize them under baseline levels.

Patent application PCT/EP2009/06828 also made the hypothesis that the more anti-HMGB1 antibodies in sera, the less serum viral load. However, this hypothesis has not been confirmed in a thorough analysis of the experiments performed and in a greater cohort of patients. Indeed, the correlation established between anti-HMGB1 antibodies and serum viral load disclosed in patent PCT/EP2009/06828 was further shown to derived from an improper statistical analysis of the results derived from a cohort of patients encompassing both untreated patients and treated patients (treatment having an effect on the viral load).

DESCRIPTION OF THE INVENTION

The present invention addresses the question of methods based on the quantitation of HMGB1 and anti-HMGB1 antibodies, to monitor HIV infection and in some cases to monitor viral load, as well as the question of the possible implication of HMGB1, anti-HMGB1 antibodies, and chemokines in prognostic method of occurrence of AIDS and neurological disorders associated with AIDS or HIV infection and in diagnostic methods in HIV-infected patient. More generally, the invention also relates to prognostic methods of either the state of progression of neurological disorders or the state of progression toward neurological disorders based on quantitation of HMGB1, anti-HMGB1 antibodies, and optionally chemokines and to diagnostic methods. Finally, the invention also relates to an in vitro prognostic method of the state of progression of a disease or a disorder in which HMGB1 is shown to be involved (e.g., in which the HMGB1 level is higher than the HMGB1 level in a healthy patient or healthy population), based on the quantitation of anti-HMGB1 antibodies, and optionally chemokines.

HMGB1 is a well-known protein appearing in the nucleus and is also known to be a cytokine. Physical and functional characteristics of HMGB1 are disclosed by and incorporated by reference to Lotze, et al., Nature Reviews, Immunology 5:351 (2005).

Antibodies which bind to HMGB1 are known and can be produced by methods well-known in the art. An example of commercially available anti-HMGB1 antibodies are Rabbit primary polyclonal antibodies to human HMGB1 (Abcam ref. 18256) which are directed against a KLH-conjugated synthetic peptide derived from residues 150 to C-terminus of human HMGB1. These methods include those which produce polyclonal antibodies to HMGB1 and monoclonal antibodies to HMGB1 or to specific fragments of HMGB1. Antibodies used in therapeutic applications have the characteristic to be blocking, e.g., especially they interfere with HMGB1-induced HIV replication in infected dendritic cells. These antibodies are preferably derived from the same species as the subject to which they are administered and recognize or are induced to the HMGB1 of the same species to which they will be administered. These antibodies may have different isotypes, such as IgA, IgG or IgM isotypes. Antibody fragments which bind HMGB1 may also be employed, including Fab, $Fab_2$, and single chain antibodies or their fragments.

The invention concerns an in vitro method for quantitating antibodies, especially total antibodies, specific for HMGB1 contained in a cerebrospinal fluid sample obtained from a subject, comprising (a) if the antibodies to be quantitated are total antibodies, treating the cerebrospinal fluid sample by an acid treatment to dissociate the immune complexes involving HMGB1 found in the sample, preferably with glycine 1.5 M at a low pH; (b) in any case contacting said, optionally treated, biological sample with native HMGB1 protein or derivatives thereof; and (c) quantitating the antibodies, especially total antibodies, specific for HMGB1.

The expression "cerebrospinal fluid" or "CSF" refers to the fluid that occupies the subarachnoid space and the ventricular system around and inside the brain. The CSF occupies the space between the arachnoid mater and the pia mater. It constitutes the content of all intra-cerebral ventricles, cisterns, and sulci as well as the central canal of the spinal cord. CSF is usually obtained by lumbar puncture.

In a preferred embodiment, the acid treatment consists to put in contact the cerebrospinal fluid sample with an acidic dissociation solution, having a low pH, preferably between pH 1 and 3, chosen to separate the HMGB1 protein from antibodies to which it is immunologically bound in the cerebrospinal fluid sample, without altering binding ability of this antibody. In a particular embodiment, the acidic dissociation solution is glycine (e.g. 1.5 M) at a low pH, preferably between pH 1 and 3 (e.g. 1.85). The acid treatment is then stopped with a neutralization buffer (such as Tris, for example 1.5 M Tris, pH 9). In another preferred embodiment, in combination with the previous one or not, the incubation with the acidic dissociation solution is carried out at a temperature between 20 and 37° C., preferably at 25° C., and/or the neutralization step takes place in ice.

In the present application, the term "quantitating" encompasses the term "quantifying" and any suitable informative determination of the HMGB1 protein or specific antibodies.

By "circulating", it is meant the residual antibodies found in the sample, in particular in the serum or the CSF, i.e., the antibodies that are found in a non-complexed form (with the protein HMGB). The term "circulating" also applies to the residual HMGB1 protein quantitated without treatment.

By "total", it is meant the sum or combined amount of circulating antibodies and immunologically complexed antibodies.

All the methods disclosed in the present application and implemented in the CSF may be carried out by analogy, i.e. similarly on other biological samples, and in particular on serum, blood, plasma, saliva or tissue.

In a particular embodiment, the invention also relates to an in vitro method for monitoring the HIV infection by quantitating the antibodies specific for High Mobility Group Box I (HMGB1), especially total antibodies specific for HMGB1, contained in a fluid sample(s) which is either a serum sample or a cerebrospinal fluid sample or in both samples obtained from a subject infected with a HIV, comprising:
a) contacting said fluid sample(s) with native HMGB1 protein or derivatives thereof; and
b) quantitating the antibodies specific for HMGB1, wherein the quantity of detected anti-HMGB1 antibodies correlates with the prognosis of the infection, in particular wherein said correlation is independent from the viral load in said subject.

The treatment step disclosed herein to prepare the total antibodies specific for HMGB1 in the cerebrospinal fluid sample applies similarly to obtain such antibodies from the serum sample.

The methods of the invention are suitable for monitoring the condition of a subject infected with a HIV, especially HIV-1 or HIV-2. In a particular embodiment, the methods of the invention are implemented in a patient infected by HIV which is under retroviral therapy and/or is an aviremic patient (i.e., 40 copies HIV RNA/ml of blood). A patient infected by HIV which is under retroviral therapy typically shows a suppressed viral load, a moderate immune deficiency measured by CD4 counts and nadir CD4 counts, and a moderate immune activation measured by $CD8^+$ T cells expressing the activation markers CD38 and HLA-DR. For example, a HIV-infected patient who shows the clinical parameters of "all patients" group as described in FIG. 14, and more particularly a HIV-infected patient who shows a mean viral load of 1.6 $log_{10}$ copies of HIV RNA/ml (i.e., aviremic patient), and/or between 300 and 800 $CD4^+$ T cells/mm³, is typically a HIV-infected patient under retroviral therapy (HAART).

The "condition" of the subject refers to the clinical status of the subject after infection with an HIV or to the risk of this subject to progress toward AIDS or toward HIV associated neurological disorders.

The invention also relates to an in vitro method for monitoring the HIV infection in a subject who is known to be infected with HIV, comprising quantitating the antibodies specific for High mobility group box I (HMGB1) contained in a cerebrospinal fluid sample obtained from this subject, wherein the antibodies targeted for quantitation are either the total antibodies specific for HMGB1 or their circulating fraction (circulating antibodies) or their immunological complexed fraction.

The methods for monitoring the HIV infection, for evaluating the immune deficiency or for determining the level of immune activation as well as the prognostic and/or diagnostic methods disclosed herein including when said method is performed with a parallel determination of the viral load, may be based on either the quantitation of the circulating antibodies specific for HMGB1 (residual antibodies), or on the quantitation of the total antibodies specific for HMGB1 or on the quantitation of the fraction of immunological HMGB1/specific antibodies complex.

The methods for evaluating the immune deficiency or for determining the level of immune activation as well as the prognostic and/or diagnostic methods disclosed herein are based on the quantitation of antibodies specific for HMGB1, in a sample such as CSF sample and/or serum sample. For some of these methods, such as diagnosis methods, additional steps may be appropriate or required to reach a diagnostic result.

In a particular embodiment of the in vitro method for quantitating antibodies specific for HMGB1, the in vitro method for monitoring the HIV infection, methods for evaluating the immune deficiency or for determining the level of immune activation as well as prognostic and/or diagnostic methods disclosed herein, the quantitated antibodies specific for HMGB1 of a patient may be compared to the amount of antibodies specific for HMGB1 determined from a healthy population (e.g., not infected with HIV), from a population of subjects (sick or not) without observed neurological disorders (e.g., a population of HIV-infected patients with no HAND) or from a population of diseased patients classified at a particular stage of progression of this disease (e.g., stages 1 to 4 of HIV-infected patients). The quantitated antibodies specific for HMGB1 of a patient may also be compared with the amount of antibodies specific for HMGB1 determined in the same patient, at a different time or at different times; in this latter case, ratio of the quantitation values obtained may be calculated and the evolution of the amount of antibodies specific for HMGB1 may be determined. The same comparison step may also apply for the quantitation of chemokines, such as IP-10 and/or MCP-1.

In a particular embodiment, all these methods are based on (encompass) either the quantitation of circulating, so-called residual, specific antibodies or of total specific antibodies.

The quantitation of the total antibodies specific for HMGB1 may be preferred.

When the quantitation is based on the total antibodies specific for HMGB1, the methods of the invention also comprise a step suitable for dissociation of immunological complexes formed with HMGB1-specific antibodies, and for example the methods of the invention use or include the quantitation method based on the acidic treatment as disclosed above and in particular the one disclosed in the examples. When the quantitation is based on the circulating antibodies specific for HMGB1, said dissociation step is not required.

In a particular embodiment, said quantitation of the antibodies specific for HMGB1 is carried out by contacting a cerebrospinal fluid sample (obtained from a subject) with the High mobility group box I (HMGB1) protein or derivatives thereof. The contact of the cerebrospinal fluid sample with said protein as well as the quantitation of the formed complexes are carried out in vitro.

In a particular embodiment, said quantitation of the antibodies specific for HMGB1 is carried out by contacting a serum sample (obtained from a subject) with the High mobility group box I (HMGB1) protein or derivatives thereof. The contact of the serum sample with said protein as well as the quantitation of the formed complexes are carried out in vitro.

It is understood that in the methods designed for monitoring the HIV infection, in particular when accompanied by the determination of the viral load, for evaluating the immune deficiency and for determining the level of immune activation as well as the prognostic and/or diagnostic methods, of the invention, it is possible to use the sequence of the full length HMGB1 protein (mammalian origin, preferably human origin such as the one defined under Accession Number NP_002119) or any peptide (10 to 30 amino acid residues) or polypeptide (30 to 215 amino acid residues, preferably 30 to 50, or 30 to 100, or 30 to 150 residues) derived from HMGB1 (HMGB1 protein derivatives) as long as these derivatives bind to antibodies specific for HMGB1 and/or enable to quantitate the anti-HGB1 antibodies. Such derivatives are selected in the group consisting of a recombinant HMGB1 (e.g. the protein commercialized as HMG biotech HM-115), an immunologically reactive part of HMGB1, an immunologically reactive part of HMGB1 whose sequence is common to HMGB1 proteins of various origins. Such an example is the recombinant BOXB from HMGB1 corresponding to the sequence common to human and mouse of HMGB1 (HMG-biotech HM-051).

By "HIV-infected patient" or "a subject who is known to be infected with HIV", it is meant a subject or patient who has been positively and accurately diagnosed for a HIV virus, and for whom HIV-infection has been confirmed following relevant testing. HIV-infected patients may be classified according to several parameters such as viral load, CD4 T cells number or clinical symptoms of AIDS.

In patients suffering from neurological disorders, a particular classification is based on these neurological disorders associated with HIV infection, as determined by clinicians, as follows;

Stage 1, with normal NP (Neuropsychological) testing;

Stage 2, with at least 2 SD (standard deviation) below the mean in one cognitive test or at least 1 SD below the mean in more than 1 test exploring the same domain. These results define the condition of ND (neuropsychological deficit);

Stage 3, including patients with criteria for ANI (asymptomatic neurocognitive impairment); and Stage 4, including patients with MCD (minor neurocognitive disorder).

This classification may be linked to the classification proposed by Antinori et al. (Neurology. 2007 Oct. 30; 69(18): 1789-99) as follows: patients with no HAND (HIV-associated neurological disorders) include stage 1 and stage 2, whereas patients with HAND include stage 3 and stage 4.

As disclosed above detecting or monitoring HIV infection by performing detection or quantitation of HMGB1 or of anti-HMGB1 antibodies in serum samples may be accompanied by determination of viral load through well known techniques.

In a particular embodiment of the invention, determining said viral load may be achieved by performing the methods of the invention themselves, especially when the diagnosed patients is not treated for HIV infection.

The invention thus also concerns in a particular embodiment a method for monitoring the HIV viral load of a subject who is known to be infected with HIV, comprising carrying out the method of quantitation of the total antibodies specific for HMGB1, in a sample, in particular in a serum or in a cerebrospinal fluid sample, wherein the more the antibodies specific for HMGB1, the more the viral load. This approach to monitor the viral load (VL) would be relevant in a patient who is known to be infected with HIV and is not treated for this infection at the time of the viral load monitoring, or in patients whose VL is not controlled.

By "viral load", it is meant either the HIV RNA (which is derived from viral particles and present in plasma) or the HIV DNA (which is integrated in the cell genome and present in cells). In a particular embodiment, the methods of the invention based on the quantitation of antibodies specific for HMGB1 are suitable to monitor the HIV RNA viral load.

By "monitoring the HIV infection", it is meant the follow-up of the HIV infection in time. HIV infection can be assessed by various parameters such as the measurement of the viral load, CD4 T cell count, and/or clinical parameters associated with disease evolution. The progression of the HIV infection, i.e. the decrease, the increase or the stability of measured parameters, as compared to a previous assay, will dictate the way of caring the patient. The progression of the HIV infection reflects the HIV replication and/or the integration of the HIV genome into the genome of target cells.

The invention is also directed to an in vitro prognostic method of either the state of progression of Acquired immune deficiency syndrome (AIDS) or the state of progression toward AIDS, of a patient infected with HIV, or the state of progression towards neurological disorders associated with HIV infection, comprising carrying out the quantitation method or the method for monitoring HIV infection disclosed above, in a sample, in particular in a serum or in cerebrospinal fluid sample, obtained from a patient after HIV infection, and preferably during primary or acute infection, or during chronic infection and wherein the more the level of antibodies specific for HMGB1, the more the risk to develop AIDS or an advanced state of AIDS and in particular the more the risk to develop neurological disorders associated with HIV infection.

The invention is also directed to an in vitro prognostic method of the state of progression of neurological disorders or the state of progression towards neurological disorders, comprising:
a) contacting a cerebrospinal fluid sample or a serum sample or both a sample of serum and a sample of cerebrospinal fluid, obtained from said patient, with native HMGB1 protein or derivatives thereof; and
b) quantitating the antibodies specific for High Mobility Group Box I (HMGB1) contained in said cerebrospinal fluid sample, said serum sample or said both sample of serum and sample of cerebrospinal fluid
the more the level of antibodies specific for HMGB1, the more the risk to develop neurological disorders or to develop an advanced stage of neurological disorders.

In a particular embodiment, when said neurological disorders result or are suspected to result from an infection (by a pathogen, bacteria or virus), the sample is obtained either during primary or acute infection or during chronic infection.

The term "prognostic" refers to the possibility to evaluate, at the time the quantitation of the antibodies specific for HMGB1 is carried out on a sample obtained from a patient, the risk for the patient to develop or to progress toward neurological disorders, or in a HIV-infected patient, the risk to develop AIDS or to progress toward AIDS.

The invention also relates to diagnostic methods that combine (1) the evaluation in a patient of the presence of neurological disorders, or in a HIV-infected patient, the presence of neurological disorders associated with AIDS, by conventional clinical criteria; and (2) the confirmation or the correlation of the appearance of these neurological disorders by the determination of immunological parameters, in particular the quantitation of specific antibodies against HMGB1 (and optionally the quantitation of chemokines such as IP-10 and/or MCP-1), combined optionally with the determination of volumetric and/or metabolic changes. The quantitation of specific HMGB1 antibodies is carried out as described in the present application for the prognostic methods. Thus, the level of antibodies specific for HMGB1 may be correlated to the observation of conventional clinical criteria to confirm the clinical diagnosis. The terms "diagnostic" and "diagnosis" refer to the possibility to determine for a patient, at the time the quantitation of the antibodies specific for HMGB1 is carried out on a sample obtained from this patient, the presence or the absence of neurological disorders, or in a HIV-infected patient, the presence or the absence of neurological disorders associated with AIDS, by relying on both conventional clinical criteria and immunologic parameters. The quantitation of HMGB1 specific antibodies in the course of diagnostic methods is particularly appropriate in patients in which conventional clinical criteria do not enable to conclude with certainty on the appearance of neurological disorders. For example, in HIV-infected patients classified in stage 2 (neuropsychological deficit), the quantitation of HMGB1 specific antibodies may be an efficient complementary indicator to confirm, to infirm or to qualify the diagnosis of neurological disorders obtained with the conventional clinical criteria.

In a particular embodiment, the present in vitro prognostic method and/or diagnostic method are in general applicable to diseases or disorders in which HMGB1 is shown to be involved and associated with a pathological risk or condition.

Thus, the methods of the invention can be implemented:
(1) in diseases or disorders in which neurological disorders are present, whatever their origin. This category includes, but is not limited to, the diseases or disorders of infectious origin, e.g., bacterial infection, pathogen infection, viral infection or infection by prion. A particular example of infectious disorder with neurological disorders is HIV infection. This category also includes, but is not limited to, diseases or disorders the origin of which is non infectious (for example is of a traumatic origin) or the origin of which is unknown, e.g., acute neuronal injury, traumatic brain injury, Alzheimer disease, Huntington disease, postischemic brain injury, Parkinson disease, any disorder affecting the peripheral nervous system and/or the spinal chord such as spinal chord injury, amyotrophic lateral sclerosis, and demyelinating diseases such as multiple sclerosis (MS).

By "neurological disorders", it is meant for example dementia complex (ADC), encephalopathy, central nervous system lymphomas, cryptococcal meningitis, cytomegalovirus (CMV) encephalitis, encephalitis and myelitis caused by the herpes zoster virus, neuropathy (peripheral neuropathy and distal sensory polyneuropathy), neurosyphilis, progressive multifocal leukoencephalopathy (PML), toxoplasma encephalitis or cerebral toxoplasmosis and vacuolar myelopathy.

(2) in diseases or disorders without neurological disorders, in which the HMGB1 protein is shown to be involved, the origin of which being infectious (bacteria, pathogen or virus) or being autoimmune. Examples of diseases of this second category encompass, but are not limited to, type 1-diabetis, systemic lupus erythematosus (SLE), Rheumatoid Arthritis, HSV-2 infection, Chronic Hepatitis B, *Legionella* infection, Sepsis or Asthma.

More particularly, the invention is directed to an in vitro prognostic method of either the state of progression of neurological disorders associated with Acquired Immune Deficiency Syndrome (AIDS) or the state of progression toward neurological disorders associated with HIV infection or with AIDS, of a patient infected with HIV, comprising carrying out the quantitation method or the method for monitoring HIV infection disclosed above, in a sample, in particular in a serum or in a cerebrospinal fluid sample, obtained from said patient after infection, and preferably during primary or acute infection or during chronic infection, and wherein the more the level of antibodies specific for HMGB1, the more the risk to develop neurological disorders associated with AIDS or to develop advanced neurological disorders associated with AIDS or neurological disorders of an advanced stage of AIDS.

The expression "state of progression of AIDS or towards AIDS" refers to the various stages met in the progression of AIDS or toward AIDS, and in particular refers to the WHO Disease Staging System for HIV Infection and Disease produced and updated by the World Health Organisation, which is summarized hereinafter. Stage I: HIV disease is asymptomatic and not categorized as AIDS; Stage II includes minor mucocutaneous manifestations and recurrent upper respiratory tract infections; Stage III includes unexplained chronic diarrhea for longer than a month, severe bacterial infections and pulmonary tuberculosis; and Stage IV includes toxoplasmosis of the brain, candidiasis of the oesophagus, trachea, bronchi or lungs and Kaposi's sarcoma.

The expression "state of progression towards neurological disorders", when applied to a HIV-infected patient, refers to the neurological disorders stages (1 to 4) classification as described above. Alternatively, the classification proposed by Antinori et al. and referring to no HAND (HIV-associated neurological disorders) and HAND patients may also be considered.

The expression "neurological disorders associated with Acquired Immune Deficiency Syndrome" or "AIDS-associated neurological disorders" or "neurological disorders associated with HIV infection" encompasses neurological disorders of the nervous system which are caused directly by the HIV virus, by certain cancers and/or opportunistic infections, as well as disorders of unknown origin which are influenced by but are not known to be caused directly by the virus. Some of these neurological disorders associated with AIDS may be characteristic of the state of progression of the disease, as defined above. Examples of neurological disorders associated with AIDS are AIDS dementia complex (ADC) or HIV-associated encephalopathy, central nervous system lymphomas, cryptococcal meningitis, cytomegalovirus (CMV) encephalitis, encephalitis and myelitis caused by the herpes zoster virus, neuropathy (peripheral neuropathy and distal sensory polyneuropathy), neurosyphilis, progressive multifocal leukoencephalopathy (PML), toxoplasma encephalitis or cerebral toxoplasmosis and vacuolar myelopathy. Some patients with controlled viral load (VL) who are not at the AIDS stage, as for example patients under potent antiretroviral therapy (HAART) may develop neurological disorders. A clinical classification regarding these neurological disorders is disclosed above.

In a preferred embodiment of the present invention, the in vitro prognostic method of either the state of progression of neurological disorders associated with HIV infection or with Acquired Immune Deficiency Syndrome (AIDS) or the state of progression toward neurological disorders associated with HIV infection or with AIDS is performed on biological sample(s) from a patient with controlled viral load (VL) who is not at the AIDS stage, as for example a patient under potent antiretroviral therapy (HAART).

The present invention also concerns an in vitro method for evaluating the immune deficiency (or immunodeficiency) of a patient, in particular a subject who is known to be infected with HIV, comprising carrying out the quantitation method or the method for monitoring HIV infection disclosed above, in a sample, in particular in a serum or in a cerebrospinal fluid sample, obtained from said subject, wherein the more the antibodies specific for HMGB1, the more the immune deficiency is high. Regarding HIV-infected patient, the immunodeficiency observed following infection is the result of the decrease in the CD4 T cells, which have been shown in the present invention to be negatively correlated with the level of specific anti-HMGB1 antibodies.

An in vitro method for determining the level of immune activation especially persistent immune activation or persistent immune activation in some compartment(s) of the body, eliciting especially persistent inflammatory state in a patient, in particular a subject who is known to be infected with HIV, comprising carrying out the quantitation method disclosed above, in a sample, in particular in a serum or in a cerebrospinal fluid sample, obtained from said subject, wherein the more the antibodies specific for HMGB1, the more the immune activation is persistent, is also part of the present invention. The persistent (or chronic) immune activation is associated with a high expression of activation markers on CD8 T cells, in particular CD38 and/or HLA-DR markers. Therefore, the present invention has put in evidence that a high level of specific HMGB1 antibodies is correlated with high level of both $CD8^+ CD38^+$ T cells and $CD8^+ HLA-DR^+$ T cells.

Immune activation in particular refers to immune activation observed in patients in acute phase of HIV infection, or to immune activation observed in patients with chronic HIV infection, especially when said patient is not under antiretroviral treatment (ART) or is presenting neurological disorders associated with HIV infection.

Within the methods of in vitro prognostic and/or diagnostic, for evaluating the immune deficiency or for determining the level of immune activation, the quantitation method is, for example, a method comprising:

a) contacting a cerebrospinal fluid sample or a serum sample or both a sample of serum and a sample of cerebrospinal fluid, obtained from said patient, and preferably during primary or acute infection or during chronic infection, with native HMGB1 protein or derivatives thereof; and b) quantitating the antibodies specific for High Mobility Group Box I (HMGB1) contained in said cerebrospinal fluid sample, said serum sample or said both sample of serum and sample of cerebrospinal fluid, In a particular embodiment of the in vitro prognostic methods, methods for evaluating the immune deficiency or for determining the level of immune activation based on the quantitation of anti-HMGB1 antibodies, an increase of anti-HMGB1 antibodies level of above 20% compared to the level of anti-HMGB1 antibodies level in a healthy population or in a population of HIV-infected patients with no HAND is correlated with a persistent immune activation, a higher risk to develop an advanced stage of neurological disorders and/or a higher immune deficiency.

The methods of the invention may also comprise, before step a), a step suitable for dissociation of immunological complexes formed with HMGB1-specific antibodies, so that total specific anti-HMGB1 antibodies are quantitated. For example, this additional step includes an acidic treatment, such as the one disclosed in the examples. In a particular embodiment, this acid treatment consists in contacting the sample(s) (cerebrospinal fluid, serum or both) with an acidic dissociation solution, having a low pH, preferably between pH 1 and 3, chosen to separate the HMGB1 protein from antibodies to which it is immunologically bound in the sample, without altering binding ability of this antibody. In a particular embodiment, the acidic dissociation solution is glycine (e.g. 1.5 M) at a low pH, preferably between pH 1 and 3 (e.g. 1.85). The acid treatment is then stopped with a neutralization buffer (such as Tris, for example 1.5 M Tris, pH 9). The acidic treatment leads to a dilution of the biological sample (CSF, serum . . . ). In another preferred embodiment, in combination with the previous one or not, the incubation with the acidic dissociation solution is carried out at a temperature between 20 and 37° C., preferably at 25° C., and/or the neutralization step takes place in ice.

In a particular embodiment, said quantitation of the antibodies specific for HMGB1 is carried out by contacting in vitro a sample with the High mobility group box I (HMGB1) protein or derivatives thereof. Thus, said quantitation is carried out using the sequence of the full length HMGB1 protein (mammalian origin, preferably human origin such as the one defined under Accession Number NP_002119) or any peptide (10 to 30 amino acid residues) or polypeptide (30 to 215 amino acid residues, preferably 30 to 50, or 30 to 100, or 30 to 150 residues) derived from HMGB1 (HMGB1 protein derivatives) as long as these derivatives bind to antibodies specific for HMGB1 and/or enable to quantitate the anti-HGB1 antibodies. Such derivatives are selected in the group consisting of a recombinant HMGB1 (e.g. the protein commercialized as HMG biotech HM-115), an immunologically reactive part of HMGB1, an immunologically reactive part of HMGB1 whose sequence is common to HMGB1 proteins of various origins. Such an example is the recombinant BOXB from HMGB1 corresponding to the sequence common to human and mouse of HMGB1 (HMGbiotech HM-051).

Each and all the in vitro methods disclosed in the present application optionally further comprise the quantitation of other molecules found in the sample (such as the serum or the cerebrospinal fluid sample), and in particular of chemokines. Examples of chemokines that can, independently, be assayed and quantitated, are the chemokine IP-10 and the chemokine MCP-1. The human chemokine IP-10 (10 kDa interferon-gamma-induced protein) is also called Chemokine (C-X-C motif) ligand 10 or CXCL10, and is referenced under NCBI Accession Number NP_001556); the human chemokine MCP-1 (for monocyte chemotactic protein-1) is also called Chemokine (C-C motif) ligand 2 (CCL2) and is referenced under NCBI Accession Number NP_002973).

When applied to the molecules and in particular to the chemokines such as the chemokine IP-10 and the chemokine MCP-1, the term "quantitating" or "quantitation" encompasses the term "quantifying" and any suitable informative determination of the level of chemokine IP-10 and chemokine MCP-1.

In particular, the invention relates to an in vitro method for monitoring the state of a subject who is known to be infected with HIV, comprising carrying out the quantitation method disclosed herein (quantitation of antibodies specific for HMGB1) and a step to quantitate the chemokine IP-10 and/or the chemokine MCP-1, in a sample, in particular in a serum or in a cerebrospinal fluid sample, obtained from said subject.

In another embodiment, the invention is also directed to an in vitro method of prognosticating either the state of progression of neurological disorders or the state of progression toward neurological disorders or a diagnostic method, comprising carrying out, in a sample, in particular in a serum or in a cerebrospinal fluid sample or both, obtained from a patient, the quantitation method disclosed herein and steps to quantitate the chemokine IP-10 and/or the chemokine MCP-1, and wherein the more the level of antibodies specific for HMGB1 and the more the chemokine IP-10 and/or the more chemokine MCP-1, the more the risk to develop neurological disorders or to develop an advanced stage of neurological disorders.

Moreover, the invention is also directed to an in vitro method of prognosticating either the state of progression of neurological disorders associated with Acquired Immune Deficiency Syndrome (AIDS) or with HIV infection in general or the state of progression toward neurological disorders associated with AIDS or with HIV infection in general, of a patient infected with HIV, comprising carrying out, in a sample, in particular in a serum or in a cerebrospinal fluid sample, obtained from a patient after infection, the quantitation method disclosed herein (quantitation of antibodies specific for HMGB1) and steps to quantitate the chemokine IP-10 and/or the chemokine MCP-1 and wherein the more the level of antibodies specific for HMGB1 and the more the chemokine IP-10 and/or the more chemokine MCP-1, the more the risk to develop neurological disorders associated with AIDS or with HIV infection in general or to develop an advanced stage of neurological disorders associated with AIDS or with HIV infection in general.

For all the prognosis methods as described herein, steps to quantitate the chemokine(s) are particularly performed at the same time as the step to quantitate the antibodies specific for HMGB1.

The invention also concerns a method comprising the quantitation of the antibodies specific for HMGB1 (for example as described above), in the cerebrospinal fluid sample and in the serum sample of a HIV-infected individual, both quantitations being carried in the same individual and on samples taken at the same time, and, optionally, the quantitation of the chemokine IP-10 and/or the chemokine MCP-1, both in the cerebrospinal fluid sample and the serum sample of the same individual and said samples being taken at the same time.

This method, based on parallel quantitation of the antibodies specific for HMGB1 in two different samples may be used in the following applications:

an in vitro method for monitoring of the human immunodeficiency virus (HIV) infection in a subject who is known to be infected with HIV;

an in vitro prognostic method for the state of progression of Acquired immune deficiency syndrome (AIDS) or the state of progression toward AIDS, of a patient infected with HIV, and preferably during primary or acute infection or during chronic infection;

an in vitro prognostic method for either the state of progression of neurological disorders or the state of progression toward neurological disorders of a patient.

an in vitro prognostic method for either the state of progression of neurological disorders associated with Acquired immune deficiency syndrome (AIDS) or with HIV infection or the state of progression toward neurological disorders associated with AIDS or with HIV infection, of a patient infected with HIV, during primary or acute infection or during chronic infection; and when associated with other means, in a diagnostic method for either the state of progression of neurological disorders or the state of progression toward neurological disorders in a patient, in particular for either the state of progression of neurological disorders associated with AIDS or with HIV infection or the state of progression toward neurological disorders associated with AIDS or with HIV infection, in a patient infected with HIV.

By "at the same time", it is meant that the samples are obtained from a determined patient, within a period of time in which the clinical symptoms, in particular the neurological disorders, such as the neurological disorders associated with AIDS or HIV, the stage of AIDS and/or the serum or CSF viral load of said HIV-infected patients are similar (statistically not significant) or identical. In particular, this period does not exceed (is less than) 6 months, 3 months, 1 month or two weeks.

In parallel to each and all the an in vitro prognostic and/or diagnostic methods, the in vitro method for evaluating the immune deficiency, the in vitro monitoring of the condition of a patient, the in vitro method for determining the level of immune activation and the method of quantitation of the antibodies specific for HMGB1 in the cerebrospinal fluid sample and in the serum sample as disclosed above, the HIV viral load is determined using a conventional method (for example by PCR). The expression "in parallel" means that the methods are carried out in samples obtained from the same patient at the same time.

Interestingly, while the serum and/or CSF viral load of a patient may be undetectable and reveals an absence of replication of the HIV virus in blood and/or CNS, the quantitation of a large quantity of antibodies specific for HMGB1, possibly together with large quantity of the chemokine IP-10 and/or the chemokine MCP-1, reveals that the HIV virus replicates in other compartments or organs such as liver, brain or intestine. This may explain that treated HIV-infected patients having low or undetectable HIV viral load according to the known standards do not progress towards AIDS while presenting neurological disorders. This observation justifies that, in parallel to the determination of the serum viral load, other assays, such as the quantitation of antibodies specific for HMGB1, may be implemented to take into account the fact that the HIV virus infects and maintains in various organs and compartments.

The methods of in vitro prognostic and/or diagnostic may further comprise complementary assays designed to confirm or to validate the state of progression of neurological disorders or the state of progression toward neurological disorders, in particular neurological disorders associated with AIDS or HIV infection. These assays comprise:
(a) identifying volumetric changes in the basal ganglia of said patient, preferably by Magnetic Resonance Imagining measurements; and/or
(b) identifying metabolic changes in the basal ganglia of said patient, preferably by calculating the serum Choline/N-acetyl Aspartate ratio (Cho/NAA).

All the methods described herein are implemented in vitro.

The invention also concerns the use of native HMGB1 protein or derivatives thereof as defined above for the manufacture of a kit, a marker or means for the in vitro prognostic of the state of progression of neurological disorders or the state of progression towards neurological disorders of a patient, in particular a HIV-infected patient, said prognostic and diagnostic being obtained by a method comprising:
a) contacting a cerebrospinal fluid sample or a serum sample or both a sample of serum and a sample of cerebrospinal fluid, obtained from said patient, and preferably during primary or acute infection or during chronic infection, with native HMGB1 protein or derivatives thereof; and
b) quantitating the antibodies specific for High Mobility Group Box I (HMGB1) contained in said cerebrospinal fluid sample, said serum sample or said both sample of serum and sample of cerebrospinal fluid;
wherein the more the level of antibodies specific for HMGB1, the more the risk to develop neurological disorders or to develop an advanced stage of neurological disorders, in particular the more the risk to develop neurological disorders or to develop an advanced stage of neurological disorders associated with HIV infection.

The invention also concerns the use of native HMGB1 protein or derivatives thereof as defined above for the manufacture of a kit, a marker or means for evaluating the immune deficiency of a patient, in particular a subject who is known to be infected with HIV, said evaluation being obtained by a method comprising:
a) contacting a cerebrospinal fluid sample or a serum sample or both a sample of serum and a sample of cerebrospinal fluid, obtained from said subject, with native HMGB1 protein or derivatives thereof; and
b) quantitating the antibodies specific for High Mobility Group Box I (HMGB1) contained in said cerebrospinal fluid sample, said serum sample or said both sample of serum and sample of cerebrospinal fluid
wherein the more the antibodies specific for HMGB1, the more the immune deficiency is high.

The invention also relates to the use of a native HMGB1 protein or derivatives thereof as defined above for the manufacture of a kit, a marker or means for determining the level of immune activation in a patient, in particular a subject who is known to be infected with HIV, said determination being obtained by a method comprising:
a) contacting a cerebrospinal fluid sample or a serum sample or both a sample of serum and a sample of cerebrospinal fluid, obtained from said subject, with native HMGB1 protein or derivatives thereof; and
b) quantitating the antibodies specific for High Mobility Group Box I (HMGB1) contained in said cerebrospinal fluid sample, said serum sample or said both sample of serum and sample of cerebrospinal fluid
wherein the more the antibodies specific for HMGB1, the more the immune activation is persistent.

The invention also relates to the use of a native HMGB1 protein or derivatives thereof as defined above for the manufacture of a kit, a marker or means for the diagnostic methods of the invention in a patient, in particular a subject who is known to be infected with HIV.

The manufacture of a kit, a marker or means described above may also comprise, besides the native HMGB1 protein or derivatives thereof, the use of a acidic dissociation solution suitable to dissociate immunological HMGB1/anti-HMGB1 antibody complexes and/or the use of means to quantitate chemokines such as IP-10 and/or MCP-1. In a particular embodiment, the manufacture of a kit, a marker or means described above also comprises the use of the native HMGB1 protein or derivatives thereof and an acidic dissociation solution suitable to dissociate immunological HMGB1/anti-HMGB1 antibody complexes. In another embodiment, the manufacture of a kit, a marker or means described above also comprises the use a native HMGB1 protein or derivatives thereof and means to quantitate the chemokine IP-10.

Any of the in vitro methods disclosed above involving the quantitation of the antibodies specific for HMGB1 may be carried out by implementing ELISA, or other immunological detection methods, using the High mobility group box I (HMGB1) protein or derivatives thereof coated on a solid support, and optionally using secondary antibodies able to detect the HMGB1 specific antibodies.

When the quantitation of the chemokine IP-10 and/or of the chemokine MCP-1 is concerned, ELISA or any other methods known in the art may be used.

The inventors have also put in evidence that the protein HMGB1 itself can be assayed in a cerebrospinal fluid sample.

Consequently, yet another aspect of the invention involves detection of an increased concentration of HMGB1 in cerebrospinal fluid samples from HIV-infected subjects. A positive correlation between the viral load and HMGB1 concentration, in a cerebrospinal fluid sample, may also be used to monitor HIV infection. HMGB1 concentration may be quantitated with well-known diagnostic tests, such as ELISA tests. Recombinant hHMGB1, anti-hHMGB1 monoclonal antibodies and rabbit anti-hHMGB1 serum are commercially available and may used in such diagnostic tests.

The invention also relates to an in vitro method for monitoring HIV infection in a subject infected with HIV comprising quantitating High mobility group box I (HMGB1) protein contained in a cerebrospinal fluid sample obtained from said subject, in particular by contacting the biological sample from said subject infected with HIV, with antibodies that immunologically bind to High mobility group box I (HMGB1), wherein the HMGB1 protein targeted for quantitation is either the total HMGB1 protein or its circulating fraction (residual circulating HMGB1) or its immunological complexed fraction.

The invention also concerns an in vitro method for monitoring the HIV viral load of a subject known to be infected with HIV, comprising carrying out the quantitation of the HMGB1 protein in a cerebrospinal fluid sample obtained from said subject, wherein the more the HMGB1 protein, the more the viral load. By "viral load", it is meant either the HIV RNA (which is derived from viral particles and present in plasma) or the HIV DNA (which is integrated in the cell genome and present in cells). In a particular embodiment, the methods of the invention based on the quantitation of HMGB1 are suitable to monitor the HIV RNA viral load.

The methods for monitoring the HIV infection or the viral load may be implemented based on the quantitation of the circulating (residual) HMGB1, based on the quantitation of the total HMGB1 or based on the quantitation of the fraction of immunological HMGB1/specific antibodies complex.

In a particular embodiment, these methods are based on either the quantitation of circulating HMGB1 or total HMGB1. When the quantitation is based on the total HMGB1, the methods of the invention also comprise a step suitable for dissociation of immunological complexes formed with HMGB1-specific antibodies, and for example the methods of the invention use or include an acidic treatment of the cerebrospinal fluid sample.

A suitable acidic treatment comprises contacting the cerebrospinal fluid sample with an acidic dissociation solution, having a low pH, preferably between pH 1 and 3, chosen to separate the HMGB1 protein from the specific antibody without altering the HMGB1 protein and its recognition capacity by specific antibodies. In a particular embodiment, the acidic dissociation solution is glycine (e.g. 1.5 M) at a low pH, preferably between pH 1 and 3 (e.g. 1.85). The acid treatment is then stopped with a neutralization buffer (such as Tris, for example 1.5 M Tris, pH 9). In another preferred embodiment, in combination with the previous one or not, the incubation with the acidic dissociation solution is carried out at a temperature between 20 and 37° C., preferably at 25° C., and/or the neutralization step takes place in ice.

The quantitation of the HMGB1 protein may be compared to the amount of HMGB1 from a cerebrospinal fluid sample obtained from a subject not infected with HIV, or to the amount of HMGB1 from a cerebrospinal fluid sample obtained from the same subject at a different time.

The invention also concerns, for the same applications, a method comprising the quantitation of HMGB1 (for example as described above) in the cerebrospinal fluid sample and in the serum sample of a HIV-infected individual, both quantitations being carried in the same individual and at the same time, and, optionally, the quantitation of the chemokine IP-10 and/or the chemokine MCP-1, both in the cerebrospinal fluid sample and the serum sample of the same individual and at the same time.

Another aspect of the invention concerns a kit that may be used to implement one of the following applications: to monitor the human immunodeficiency virus (HIV) infection of a HIV-infected subject, to monitor the HIV viral load of a HIV-infected subject who is not under treatment for HIV infection, to carry out the prognostic of either the state of progression of Acquired immune deficiency syndrome (AIDS) or the state of progression toward AIDS of a patient infected with HIV, to carry out the prognostic of either the state of progression of neurological disorders of a patient, in particular neurological disorders associated with Acquired immune deficiency syndrome (AIDS) or with HIV infection or the state of progression toward neurological disorders of a patient, in particular neurological disorders associated with AIDS of a patient infected with HIV or with HIV infection, to evaluate the immune deficiency of a patient, in particular a HIV-infected subject, to determine the level of immune activation especially persistent immune activation in a patient, in particular a HIV-infected subject, to monitor the state of HIV-infected subject and in diagnostic methods of the invention.

This kit comprises native HMGB1 protein or derivatives thereof as defined above, and optionally an acidic dissociation solution suitable to dissociate immunological HMGB1/anti-HMGB1 antibody complexes found in the biological sample, when taken from the patient, such as defined above, and optionally means to quantitate the chemokine IP-10 and/or means to quantitate the chemokine MCP-1. Optionally, this kit may also contain a neutralization buffer, for example as defined above and/or secondary antibodies binding to and/or revealing the formation of the HMGB1/specific antibodies complex. Optionally, this kit may also contain directions for use (leaflet). In a particular embodiment, the kit comprises a native HMGB1 protein or derivatives thereof and acidic dissociation solution suitable to dissociate immunological HMGB1/anti-HMGB1 antibody complexes. In another embodiment, the kit comprises a native HMGB1 protein or derivatives thereof and means to quantitate the chemokine IP-10.

The kit is implemented to quantitate the anti-HMGB1 antibodies from any biological sample, in particular from the cerebrospinal fluid sample of a HIV-infected patient or from the serum sample of a HIV-infected patient, or when parallel quantitation is required from both the cerebrospinal fluid sample and the serum sample of said HIV-infected patient.

C—Same comparisons than in B (stage 1 versus patients with stages 2, 3 and 4) were done for the indicated parameters. No statistical differences were found for any of these parameters.

Figure 13:
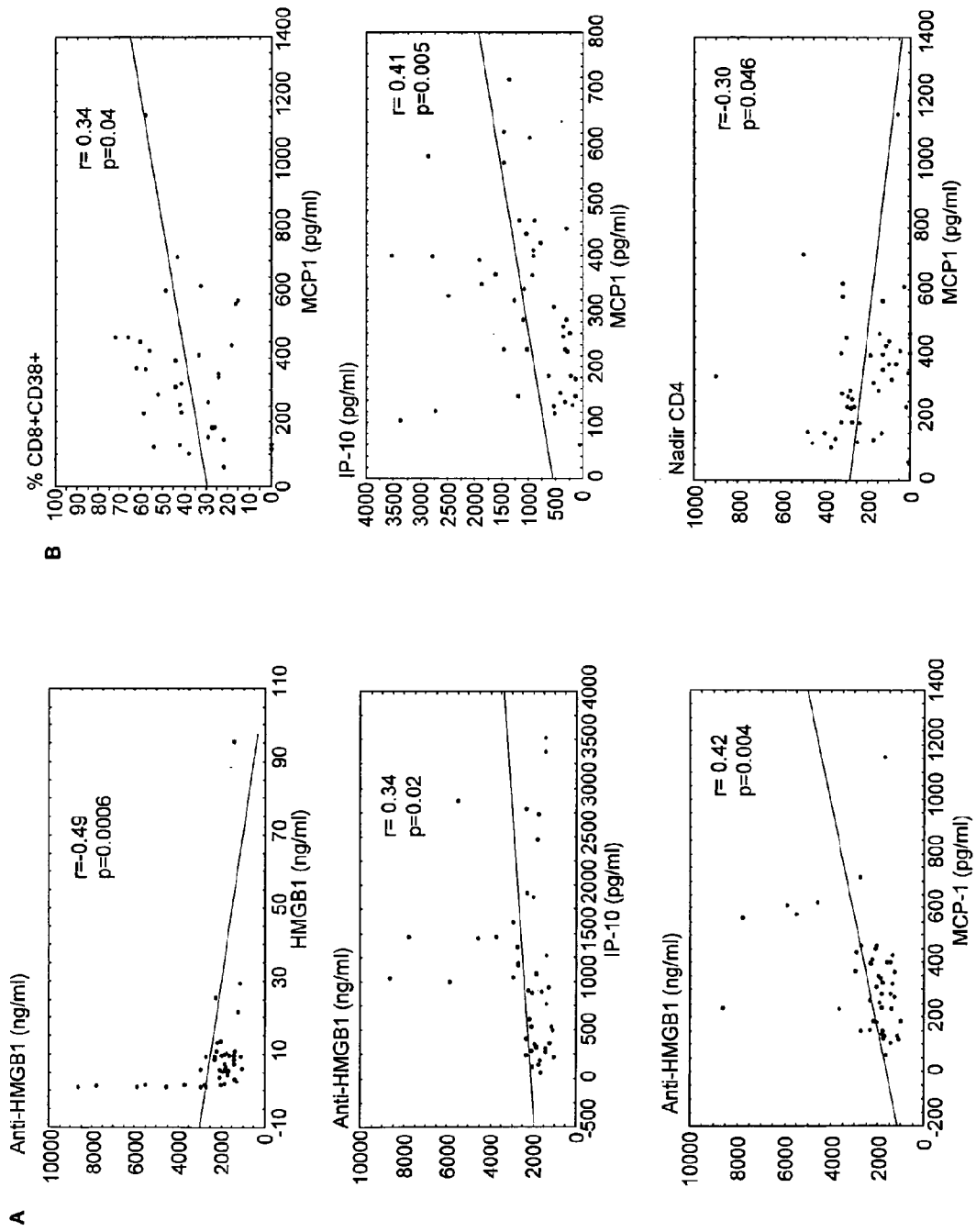
Figure 13:
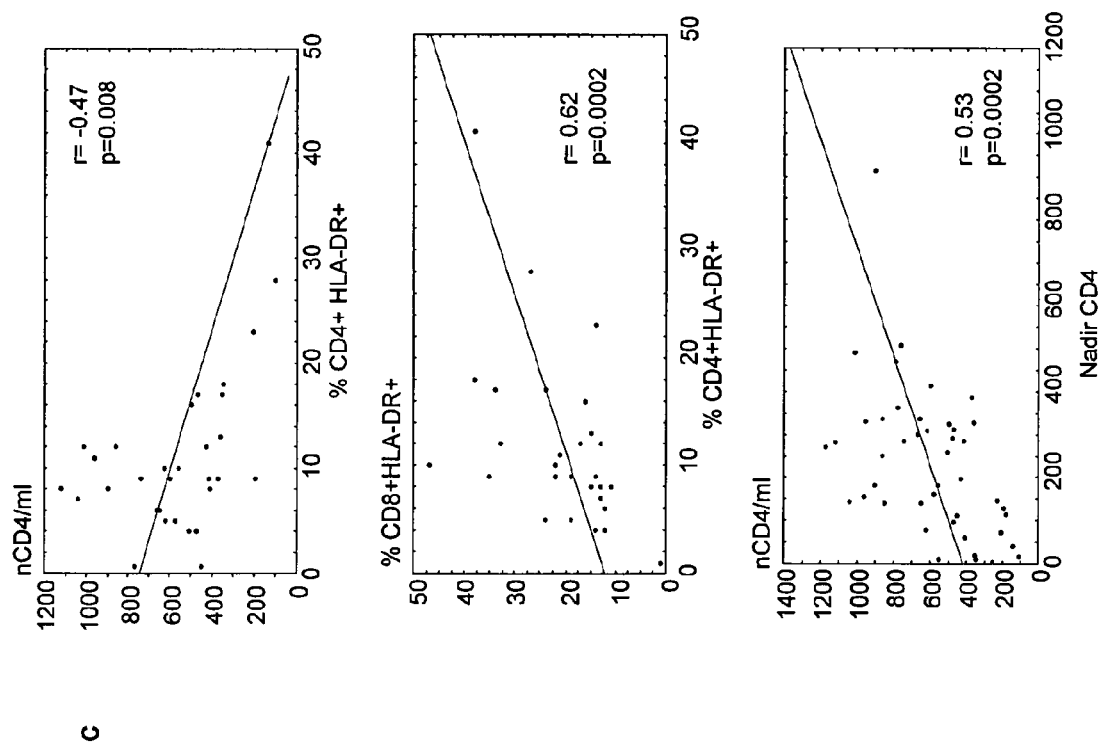

FIG. 13: Correlations between anti-HMGB1, MCP1, IP-10 and immune activation in patients with stages 2, 3 and 4 and suppressed viral load. A, B, C—Spearman correlations between indicated parameters in sera from 45 HIV+ patients with stages 2, 3 and 4 and VL<40 cp/ml. The coefficients of correlation (r) and p values are reported.

FIG. 14: Clinical and immunological parameters of patients included in the study. HIV-infected subjects were randomly selected among subjects above 18 years of age, regardless of CD4 cell count and viral load. Exclusion criteria were: previous diagnosis of HAND, active opportunistic infection, any history of neurological disorder. HAND was defined as mentioned in the text. HMGB1, anti-HMGB1, IP10 and MCP1 were quantified as described in present application. P value was determined with the Mann-Whitney test. P<0.05 was considered as significant.

Figure 15:
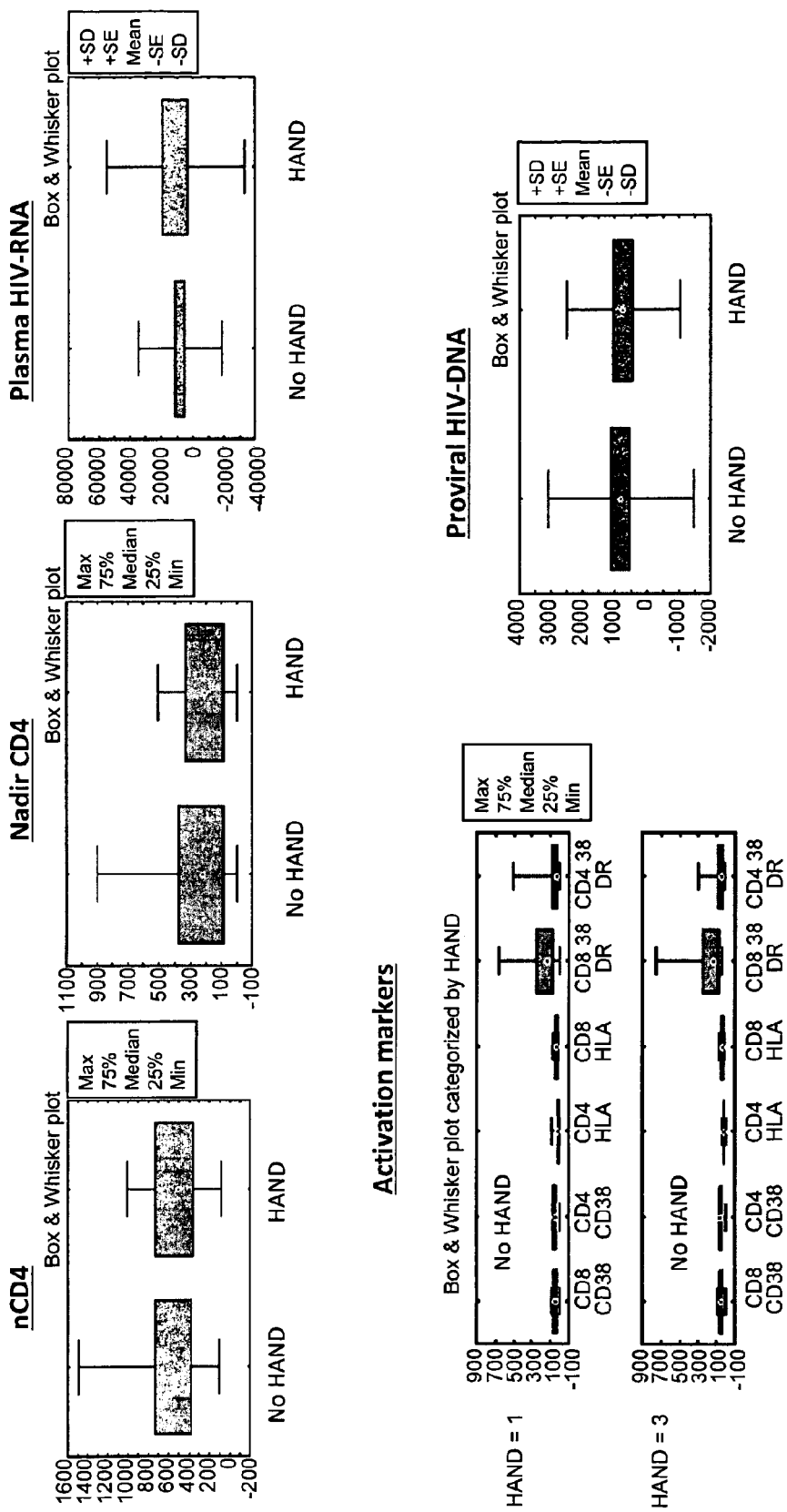

FIG. 15: HAND and no HAND patients show comparable clinical and virological parameters. For each patient, the indicated markers (CD4 count upon inclusion, nadir CD4, plasma HIV-RNA, HIV-DNA, activation markers) were recorded or quantified. These markers were compared in patients with HAND and patients without HAND. No significant differences were detected for any marker (Mann-Whitney test).

Figure 16:
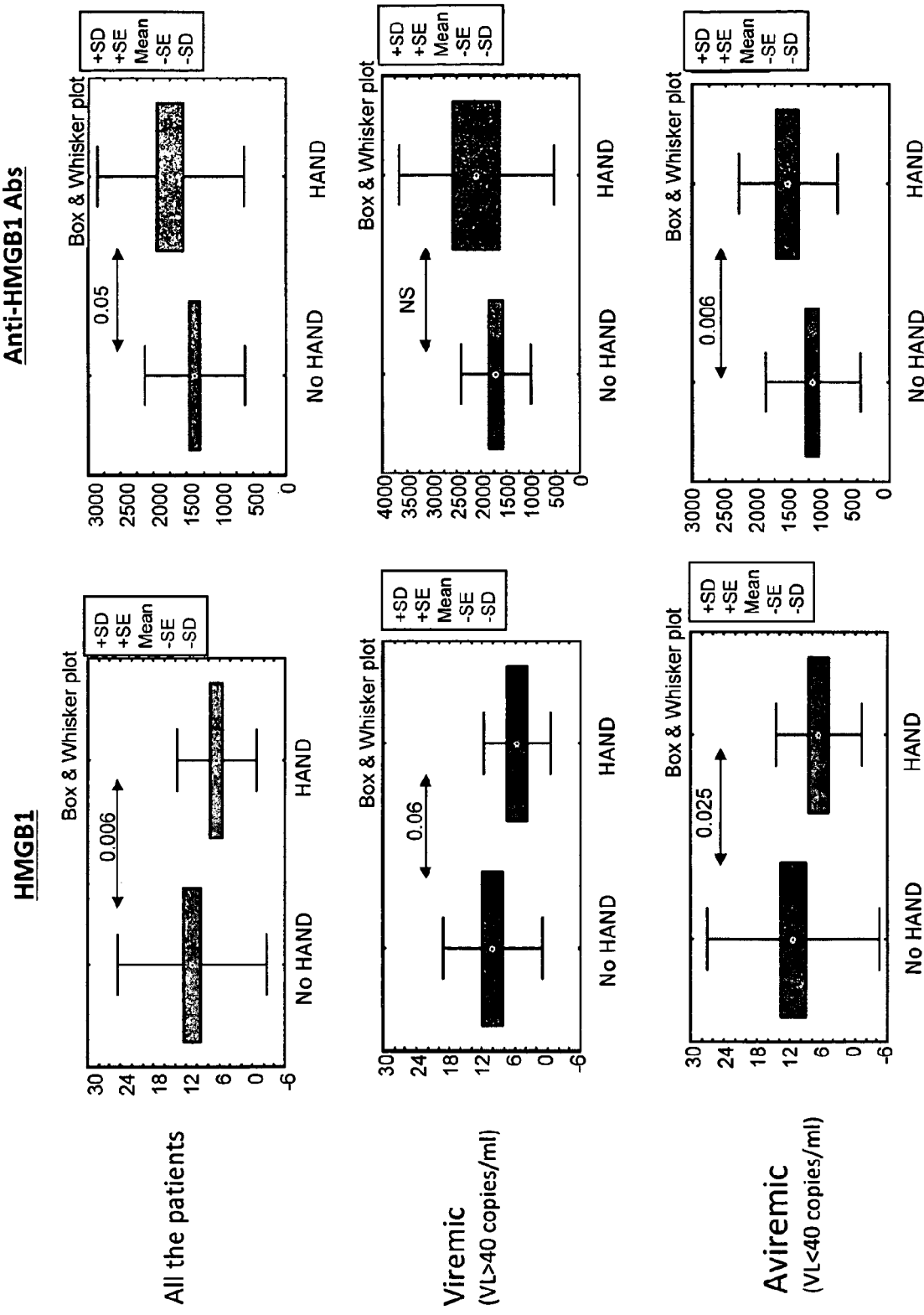

FIG. 16: HMGB1 and anti-HMGB1 levels are significantly different in viremic or aviremic HAND and no HAND patients. HMGB1 and anti-HMGB1 serum levels were quantified for all the patients according to the methods described in the present application. Their levels were compared between HAND and no HAND patients regardless their viral load, or considering only the viremic or aviremic patients. Statistical analysis was performed using the Mann-Whitney test. P<0.05 was considered as significant.

Figure 17:
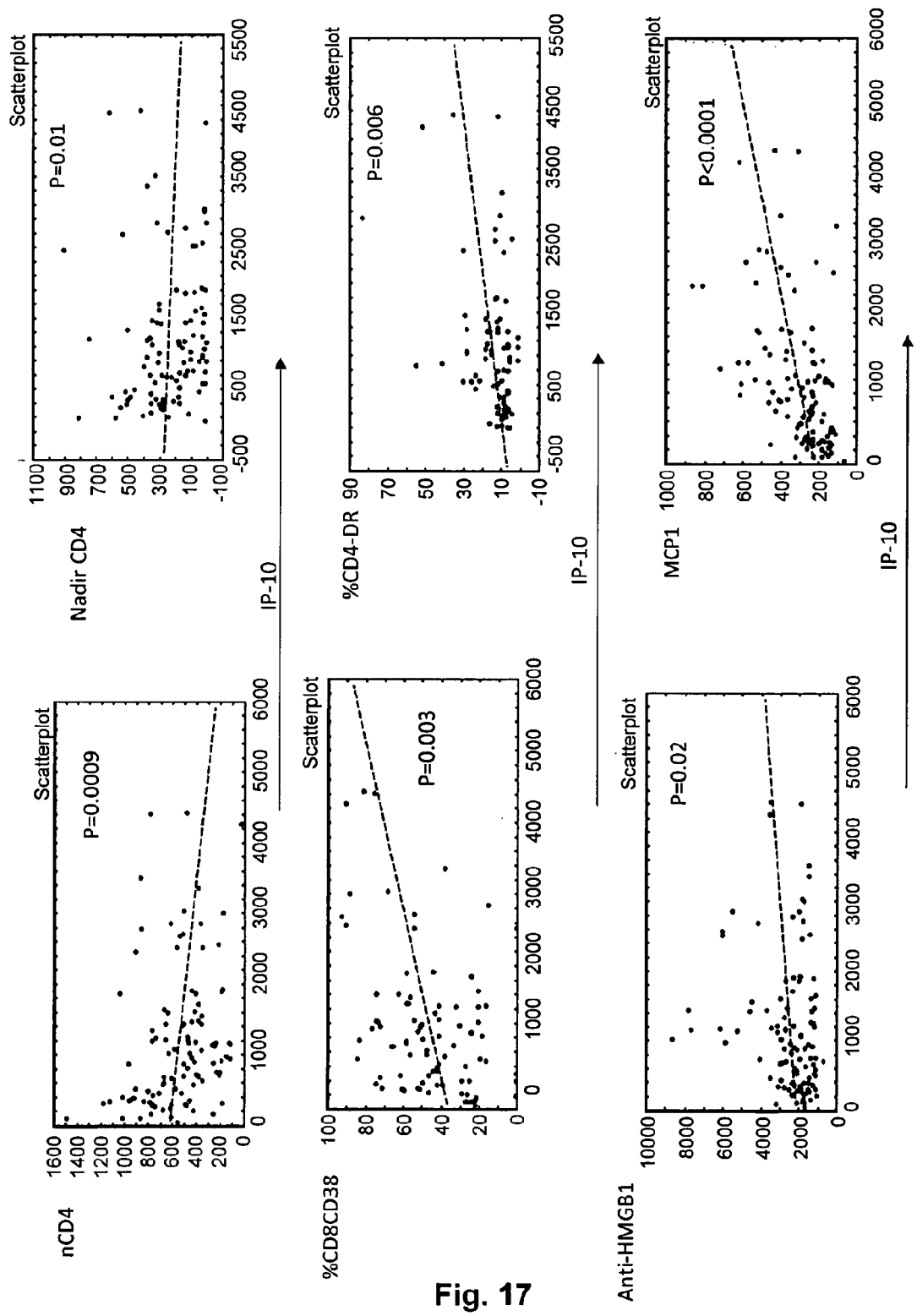

FIG. 17: Serum levels of IP-10 are correlated with immune activation, MCP1, anti-HMGB1 and nadir CD4. Correlations between serum IP10 levels and indicated immune parameters are shown. The spearman correlation test was used. P<0.05 was considered as significant.

Figure 18:
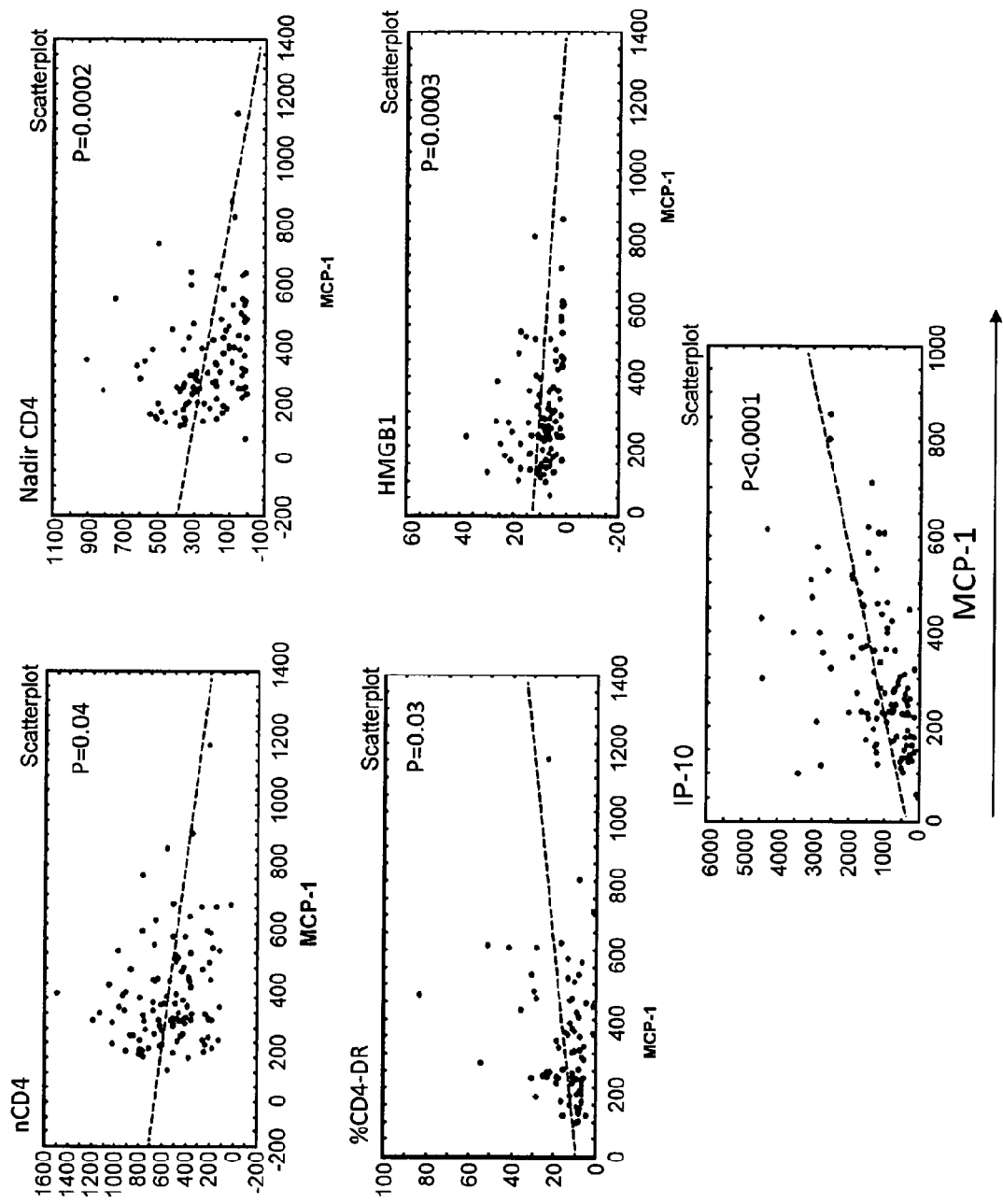

FIG. 18: Serum levels of MCP-1 are correlated with immune activation, IP-10, HMGB1 and nadir CD4. Correlations between serum MCP1 levels and indicated immune parameters are shown. The spearman correlation test was used. P<0.05 was considered as significant.

Figure 19:
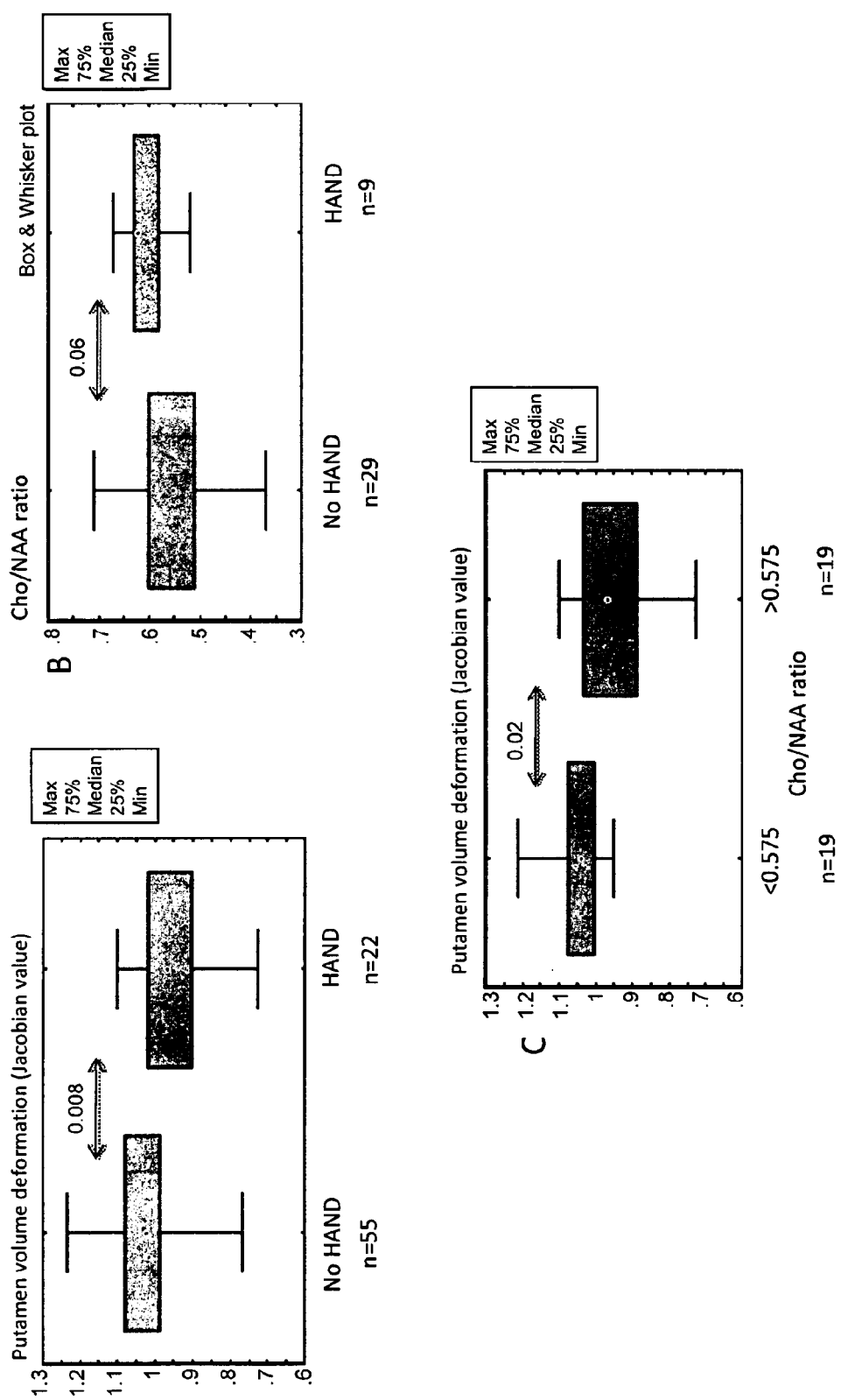

FIG. 19: Basal ganglia volumetric changes in patients with HAND and correlation with metabolic changes. Basal ganglia (BG) volumetric changes and Cho/NAA ratio were measured by MRI, as described in the specification. Patients with HAND had larger putamen (Jacobian value lower than 1) (A) and higher Cho/NAA ratios on MRI-spectroscopy of BG (B). Larger volumes of putamen were correlated to higher Cho/NAA values (p=0.02) (C).

Figure 20:
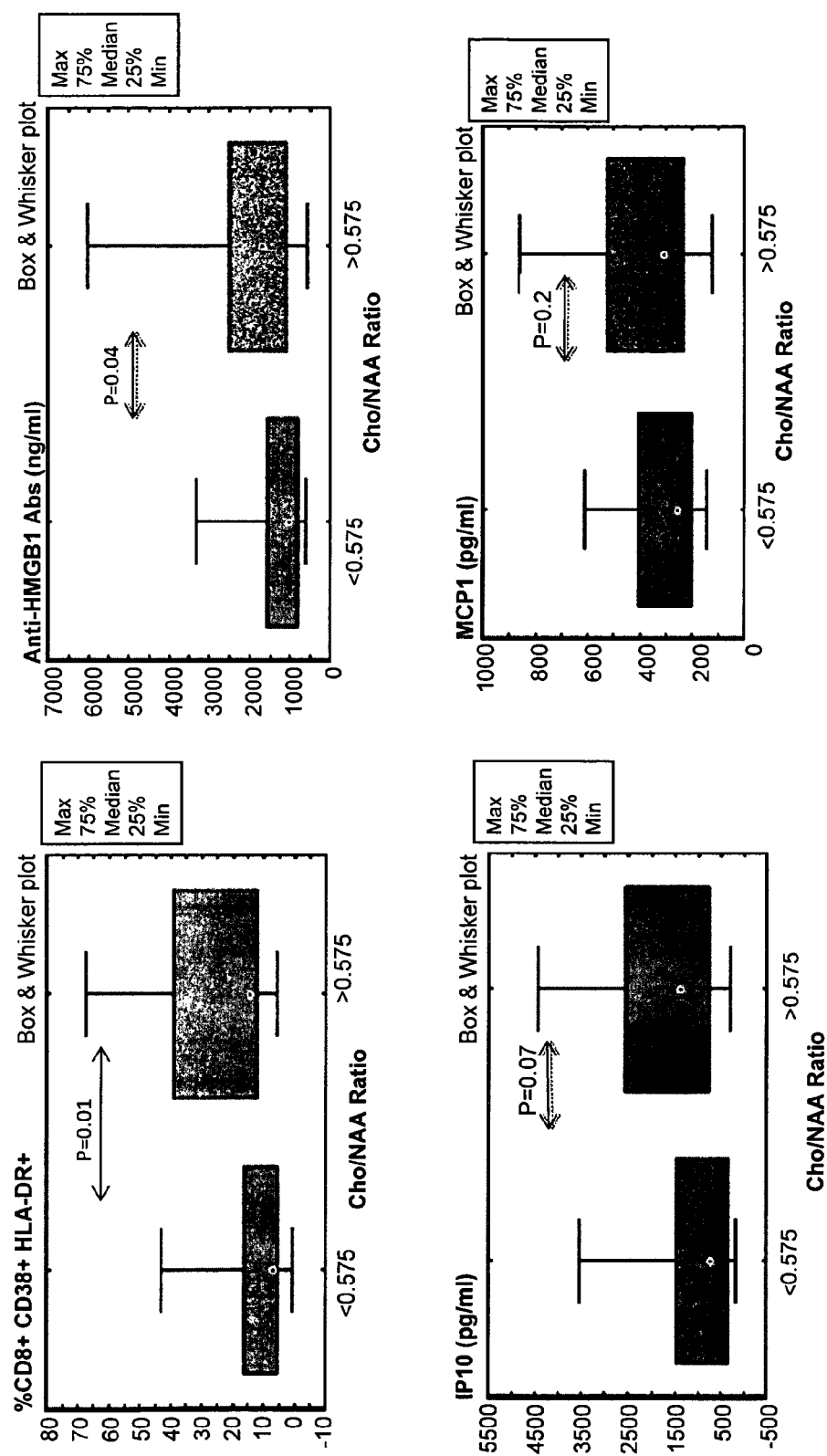

FIG. 20: Neurological impairment (Cho/NAA ratio) correlates with anti-HMGB1 Abs and IP10 levels. Increased immune activation (% CD8+CD38-HLA-DR+ T cells), and increased levels of anti-HMGB1 Abs and IP10 correlate to increased Cho/NAA values. Statistical analysis was performed using the Mann-Whitney test. P<0.05 was considered as significant.

EXAMPLES

I. Detection of HMGB1 Protein and Anti-HMGB1 Antibodies in Sample (Serum and/or Human Cerebrospinal Fluid)

The concentration of HMGB1 protein (i.e., residual circulating HMGB1 protein) in sample from HIV-infected patients was quantitated, according to the ELISA kit Shino Test (IBL).

Moreover, a specific Elisa assay for the detection of total anti-HMGB1-specific antibodies was developed. The following reagents have been used:

Rabbit primary polyclonal antibodies to human HMGB1 (Adcam ab18256) are directed against a KLH-conjugated synthetic peptide derived from residues 150 to C-terminus of human HMGB1.

Recombinant BOXB from HMGB1 (HMGBiotech HM-051) produced in *E. Coli* from an expression plasmid coding for the mammalian sequence, which is totally identical in human and mouse.

Control rabbit serum (Sigma; Ref: R9133)

anti-rabbit IgG or IgM conjugated to phosphatase alkaline (PAL), substrate p-nitrophenyl phosphate tablets (pNPP), calibrators: human IgG from serum (Sigma; ref I2511) and Human IgM from serum (Sigma; ref I8260)

Anti-human IgG (Fc specific)-alkaline phosphatase antibody produced in goat (Sigma; Ref A9544), anti-human IgM (µ-chain specific)-alkaline phosphatase antibody produced in goat (Sigma; ref A3437)

The Elisa assay, to quantitate total anti-HMGB1-specific antibodies, was carried out as follows:

Coating of 96-well plates was performed overnight at 4° C. with 0.5 µg/ml of BOXB in DPBS. Simultaneously, coating of the calibrator was performed with serial dilutions in DPBS of corresponding isotypes (only for ELISA assay carried out with human samples). Plates were washed four times with DPBS/0.05% (v/v) Tween® 20, using a microplate washer (Atlantis; Oasys). Similar washings were performed after each step of the ELISA assay. Unbound sites were blocked at 4° C. for 2 hours with PBS/2% (w/v) BSA. 100 µl aliquots of sample diluted in DPBS/0.05% (v/v) Tween®/1% (W/V) BSA were added to coated and uncoated wells and incubated for 1 hour at 37° C. All samples have been tested treated with 1.5 M Glycine (v/v, pH 1.85) for 30 mn at 25° C. in a water bath, and further kept on ice and diluted with 1.5 M Tris, v/v, pH 9.0. Samples were then immediately diluted (from 1/10 to 1/1000) and distributed on coated plates. Anti-rabbit IgG phosphatase alkaline-conjugated antibodies (ratio 1/10000), or goat anti-human IgG (ratio 1/2000), or IgM (ratio 1/2000) alkaline phosphatase-conjugated antibodies diluted in DPBS/0.05% (v/v) Tween®/1% (W/V) BSA were added for 1 hour at 37° C. Detection of antigen-specific antibodies was performed after 30 mn of incubation at 37° C. with 100 µl pNPP substrate and the reaction was stopped by addition of 100 µl NaOH 3 M. Concentration of BOXB-specific antibodies has been calculated according to the standard curve obtained from standard immunoglobulin solution absorbance by Ascent software, ThermoElectrocorp, as we previously reported in an Elisa specific for Shigella LPS (Launay et al. *Vaccine* 2009, 27:1184-1191). The data are expressed in ng/ml of antibodies detected.

II. Analysis of HMGB1 and Specific Anti-HMGB1 Antibodies, as Well as Chemokine Signatures in CSF from HIV-Infected Patients HIV-Infected Patients The group of patients analyzed for CSF content in HMGB1 and in anti-HMGB1 antibodies, is part of a cohort of 105 chronically HIV-infected patients, classified according to AIDS-associated neurological disorders (as explained above). Group 1 includes HIV-1-infected patients without neurological disorders, whereas group 2, 3 and 4 include patients with increasing neurocognitive disorders.

Figure 1:
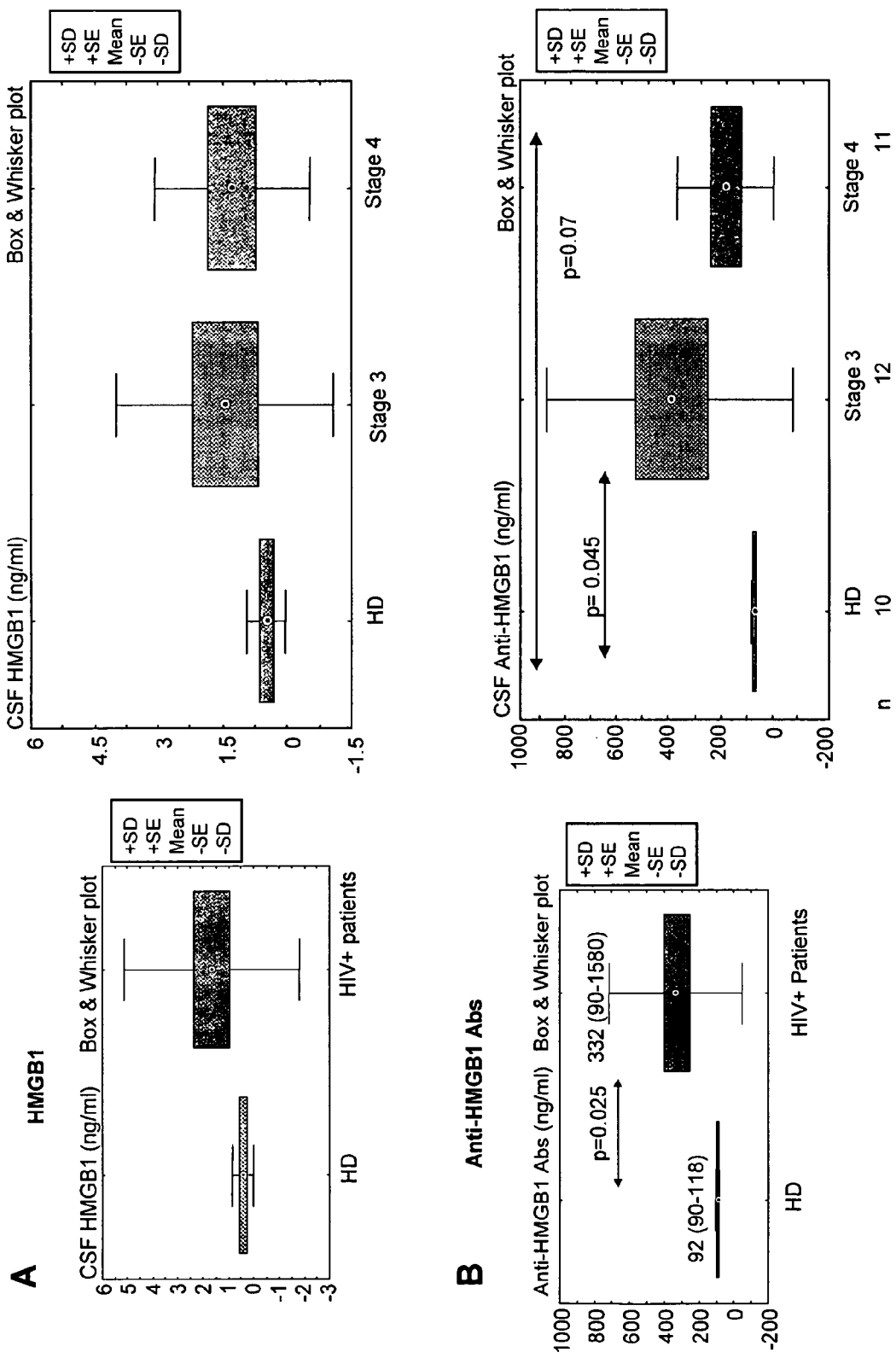
FIG. 1: Detection of HMGB1 and anti-HMGB1 antibodies in CSF from HIV-1-infected patients. A—Left Panel. HMGB1 concentration was quantitated by Elisa (Shinotest, IBL), in CSF from 10 healthy donors (HD) and 23 HIV-1-infected patients with neurological disorders. Box and Whisker Plots represent the mean±SD of CSF HMGB1 concentration (limit of detection 0.25 ng/ml) in the two groups [0.5 ng/ml (range 0.25-1.47) in HD vs 1.67 ng/ml (range 0.25-15.9) in patients]. A—Right panel. HIV-infected patients were stratified from stage 2 to stage 4 according to neurological disorder severity, CSF being obtained for stage 3 and stage 4 patients only. HMGB1 was detected at increased concentrations in CSF from stage 3 patients vs HD, but due to the variability of the values, the differences between HD and patients from both groups were not statistically significant. B—Left Panel. Anti-HMGB1 Abs concentration was quantified by Elisa in CSF from 10 healthy donors (HD) and 23 HIV-1-infected patients with neurological disorders. Box and Whisker Plots represent the mean±SD of CSF anti-HMGB1 concentration (the mean and range values are indicated on the boxes). The p value of significant differences is reported (non-parametric Mann-Whitney test). B—Right panel. CSF of stage 3 (n=12) and stage 4 (n=11) patients were tested for anti-HMGB1 Abs and compared to HD (n=10). Box and Whisker Plots represent the mean±SD of anti-HMGB1 concentration. The p value of significant differences is reported (non-parametric Mann-Whitney test).

IIa. Correlation of HMGB1 and Specific Anti-HMGB1 Antibodies with Viral Load, Disease Evolution and Chemokine Signatures Increased Levels of HMGB1 and Anti-HMGB1 Abs in CSF Sample from HIV-Infected (HIV+) Patients as Compared to Healthy Donors Using the Shinotest Elisa (IBL) assay for HMGB1 detection (limit of detection 0.25 ng/ml) and our home made Elisa assay for anti-HMGB1 antibody detection (limit of detection 90 ng/ml), increased levels of both HMGB1 (FIG. 1A) and anti-HMGB1 antibodies (FIG. 1B) have been found in CSF from HIV-infected patients (P) as compared to healthy donors (HD). The increased level of HMGB1 in patients' CSF was not statistically different to that of HD (FIG. 1A) whereas the levels of anti-HMGB1 antibodies were significantly increased compared to HD (FIG. 1B). Stratification of patients according to their neurological stage showed that increased levels of both HMGB1 and anti-HMGB1 antibodies in CSF were observed for patients in stage 3 and 4. Only anti-HMGB1 antibodies levels were statistically different from those of HD (FIG. 1).

HMGB1 and Anti-HMGB1 Antibodies from CSF Sample Correlate with Viral Load

Figure 2:
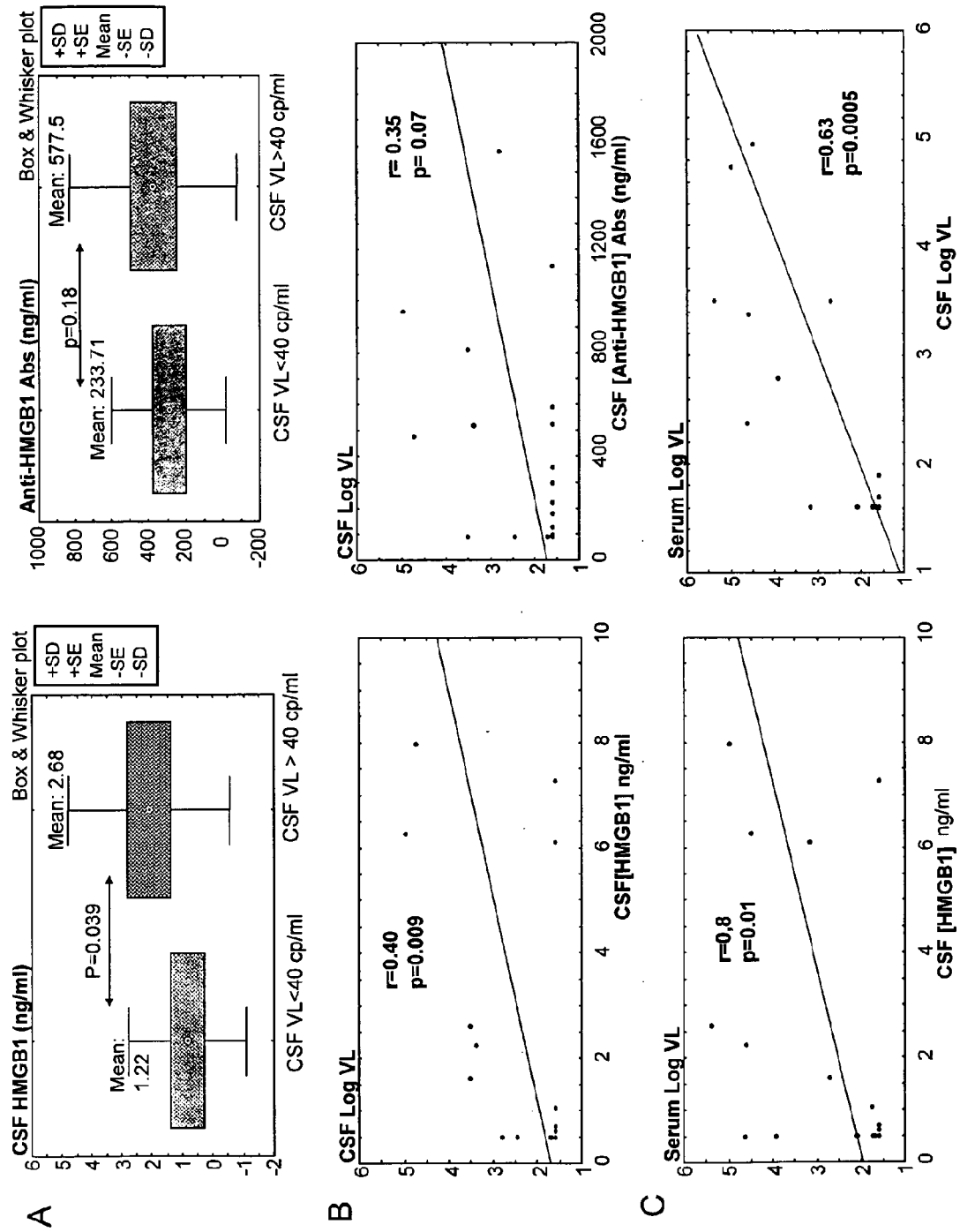
FIG. 2: Impact of viral load on HMGB1 and anti-HMGB1 antibody levels in CSF. A—Patients were stratified into 2 groups according to CSF viral load (VL): undetectable (i.e., <40 copies/ml) and positive (VL>40 copies/ml). Mean values are indicated on each box. HMGB1 and anti-HMGB1 concentrations were compared between these 2 groups and p values are reported (non-parametric Mann-Whitney test). B—Spearman correlations between CSF concentrations of either HMGB1 or anti-HMGB1 antibodies and CSF Log VL. The coefficient of correlation (r) and p values are reported. C: Spearman correlations between plasma VL and CSF HMGB1 concentration (left panel) or CSF VL (right panel). The coefficient of correlation (r) and p values are reported.

HIV-1 is probably driving the production of HMGB1 and anti-HMGB1 antibodies in CSF. This is suggested by the higher level of both molecules in patients with uncontrolled viral load (VL) compared with patients with undetectable VL (<40 cp/ml CSF) (FIG. 2A). In addition, HMGB1 and anti-HMGB1 antibody levels were found positively correlated with HIV-1 VL in CSF (FIG. 2B). As a corollary (considering that CSF VL is strongly correlated with plasma VL, FIG. 2C), CSF HMGB1 level was positively correlated with plasma VL (FIG. 2C).

CSF Anti-HMGB1 Levels Correlate with Disease Evolution

Figure 3:
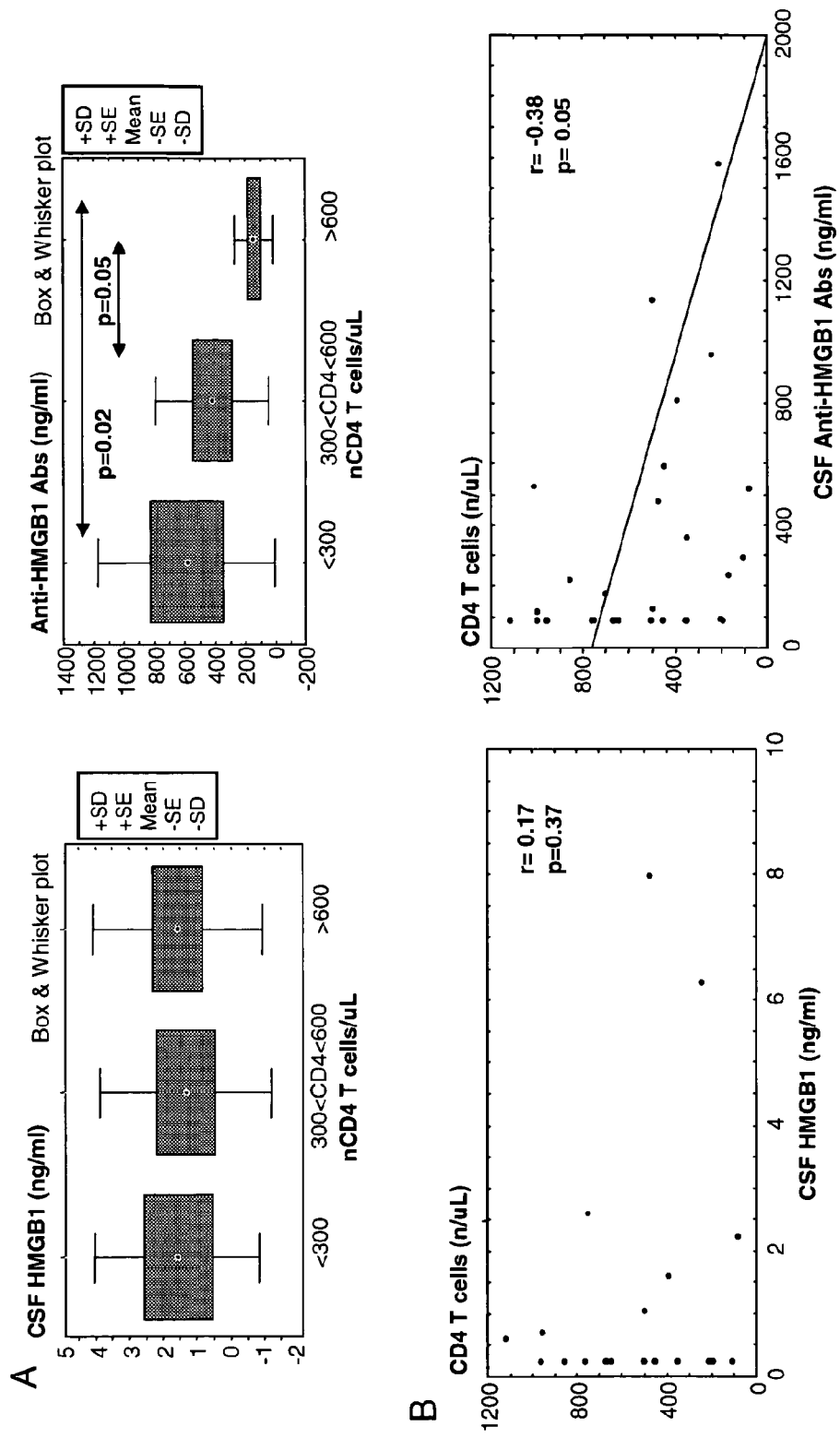
FIG. 3: Correlation of Anti-HMGB1 antibody levels in CSF with disease evolution. A—Peripheral CD4 T cell number is a correlate of disease evolution. Patients were stratified into 3 groups according to their blood CD4 T cell numbers, and HMGB1 and anti-HMGB1 antibody levels were compared between the 3 groups. p values (non-parametric Mann-Whitney test) are reported. B—Spearman correlations between CSF concentrations of either HMGB1 or anti-HMGB1 Abs and CD4 T cell numbers. The coefficients of correlation (r) and p values are reported.

The hallmark of HIV infection is the progressive disappearance of CD4 T cells in the blood, and the peripheral number of CD4 T cells is a marker of HIV disease progression. FIG. 3 A (right panel) shows that the level of anti-HMGB1 antibodies in CSF is increasing when CD4 T cell numbers are decreasing, and it is significantly higher in patients with low (<300) versus high (>600) CD4 T cell numbers. Moreover, the level of anti-HMGB1 antibodies in CSF appears to be a correlate of disease evolution, as anti-HMGB1 antibodies negatively correlate with CD4 T cell numbers (FIG. 3B right panel). Regarding HMGB1 levels in CSF, they do not vary with CD4 T cell numbers (FIGS. 3A, 3B left panels). It is noteworthy that the assay that was used for HMGB1 quantification (Shinotest, IBL) only detects residual free HMGB1 (i.e., not HMGB1 complexed with antibodies), while the assay developed in our laboratory for anti-HMGB1 antibody quantification detects the total antibodies, including the ones that are complexed to HMGB1. Thus the levels of anti-HMGB1 antibodies (1000 fold more than HMGB1) represents a more accurate measure of disease evolution than residual HMGB1.

Figure 4:
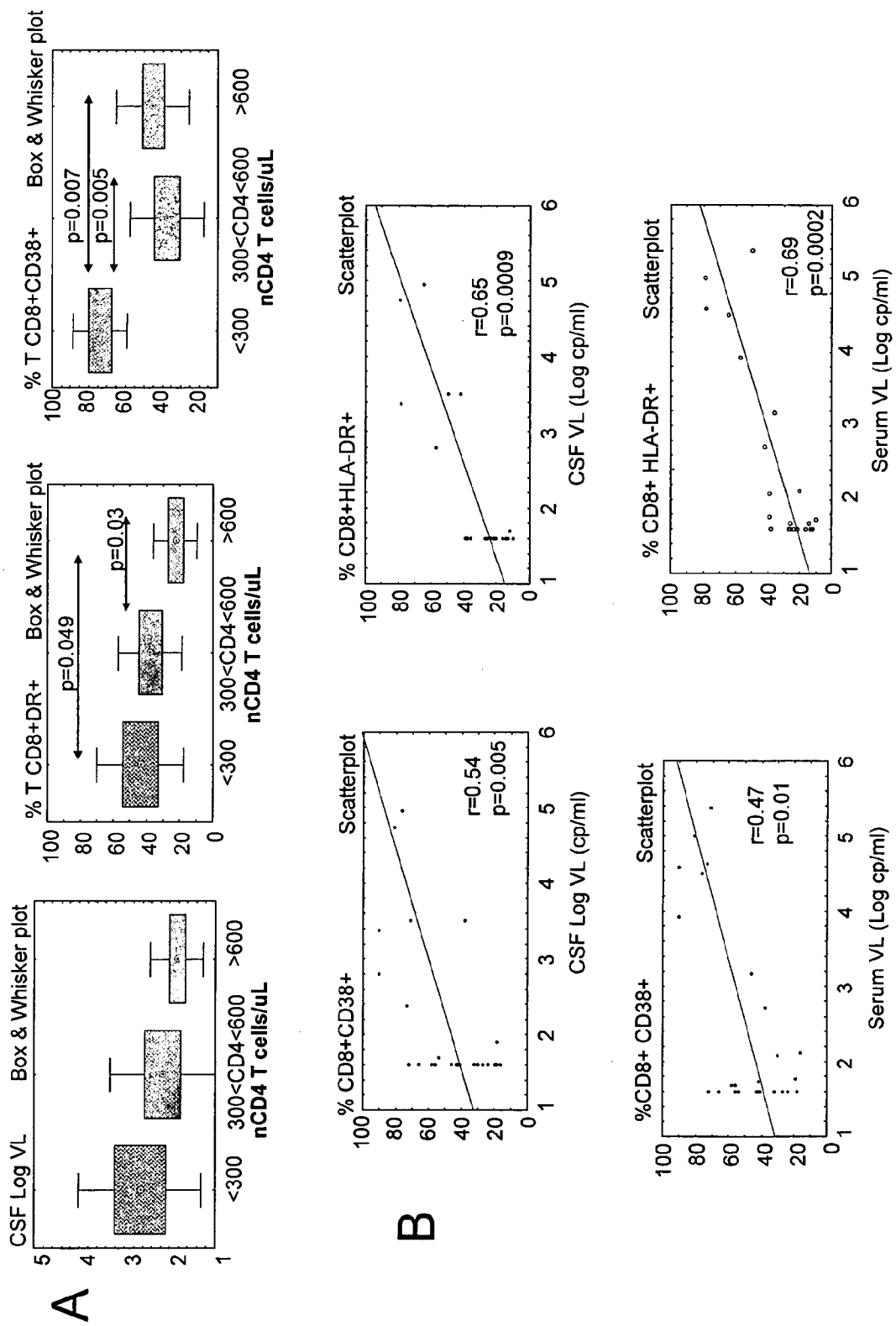
FIG. 4: Correlation of CSF HMGB1 and antiHMGB1 antibody levels with immune activation. A—CSF VL, the % T $CD8^+$ $HLA-DR^+$ and T $CD8^+$ $CD38^+$ were compared among the three groups of patients stratified according to their CD4 T cell number. p values are reported (non-parametric Mann-Whitney test). B—Spearman correlations between CSF or serum VL and the % of $CD8^+$ $CD38^+$ T cells or CD8+ HLA-DR+ T cells. The coefficients of correlation (r) and p values are reported. C—Top panel: Spearman correlations between CSF anti-HMGB1 antibodies and the % of $CD4^+$ $HLA-DR^+$ T cells, or $CD8^+$ $HLA-DR^+$ T cells. Bottom panel: Spearman correlations between CSF HMGB1 and the % $CD8^+$ $HLA-DR^+$ T cells. The coefficients of correlation (r) and p values are reported.
Figure 4:
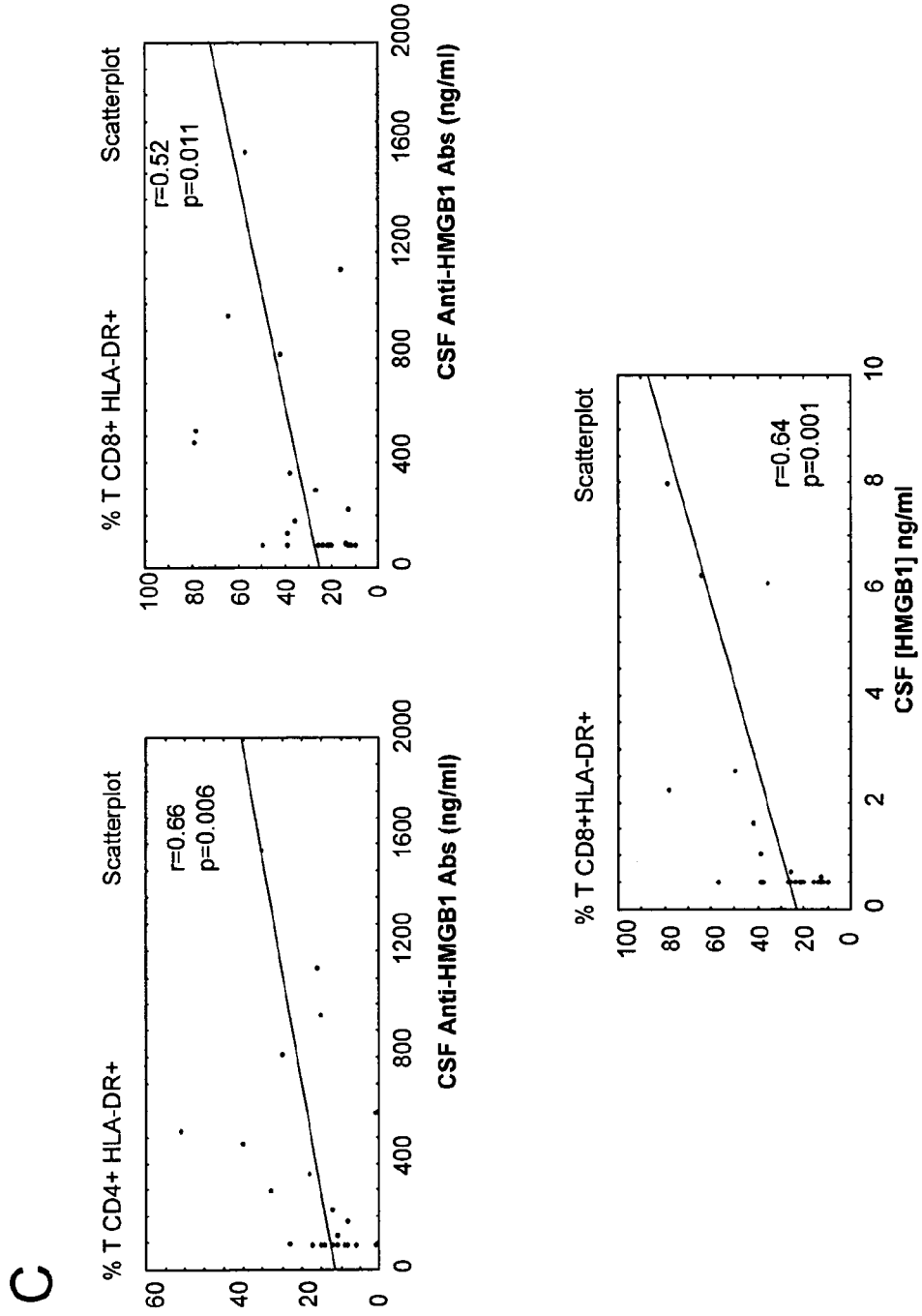

CSF HMGB1 and Anti-HMGB1 Antibody Levels are Associated with a Persistent Immune Activation A number of studies have demonstrated that chronic HIV-infection induces a state of immune activation which is a strong marker of disease progression (Giorgi JV, et al. Shorter survival in advanced HIV-1 infection is more closely associated with T lymphocyte activation than with plasma virus burden or virus chemokine coreceptor usage. J Infect Dis 1999). Immune activation can be analyzed through the expression of activation markers on blood CD8 T cells, in particular CD38 and HLA-DR, whose combination is associated with the risk of progression to AIDS (Liu Z, et al. Elevated CD38 antigen expression on CD8+ T cells is a stronger marker for the risk of chronic HIV disease progression to AIDS and death in the MACS Study than CD4+ cell count, soluble immune activation markers, or combinations of HLA-DR and CD38 expression. J Acquir Immune Defic Syndr Hum Retrovirol 1997; 16:83-92). FIG. 4A shows that the percentages of CD8+CD38+ T cells is significantly increased in patients with low CD4 T cell numbers (CD4 <300/uL) compared to patients with high numbers (>600/uL), and the activation state of T cells (i.e., the percentage of CD8+CD38+ T cells and CD8+HLA-DR+ T cells) is positively correlated with both CSF and plasma viral load (FIG. 4B). In that context it is noteworthy that the expression of HMGB1 and anti-HMGB1 antibodies is positively correlated with the activation state of T cells (FIG. 4C).

Therefore, HMGB1 and anti-HMGB1 detection in CSF of patients with neurological disorders is the consequence of persistent immune activation driven by HIV.

Increased Levels of HMGB1 and Anti-HMGB1 Antibodies in CSF Sample are Associated with Increased Levels of Inflammatory Chemokines IP-10 and MCP-1.

Figure 5:
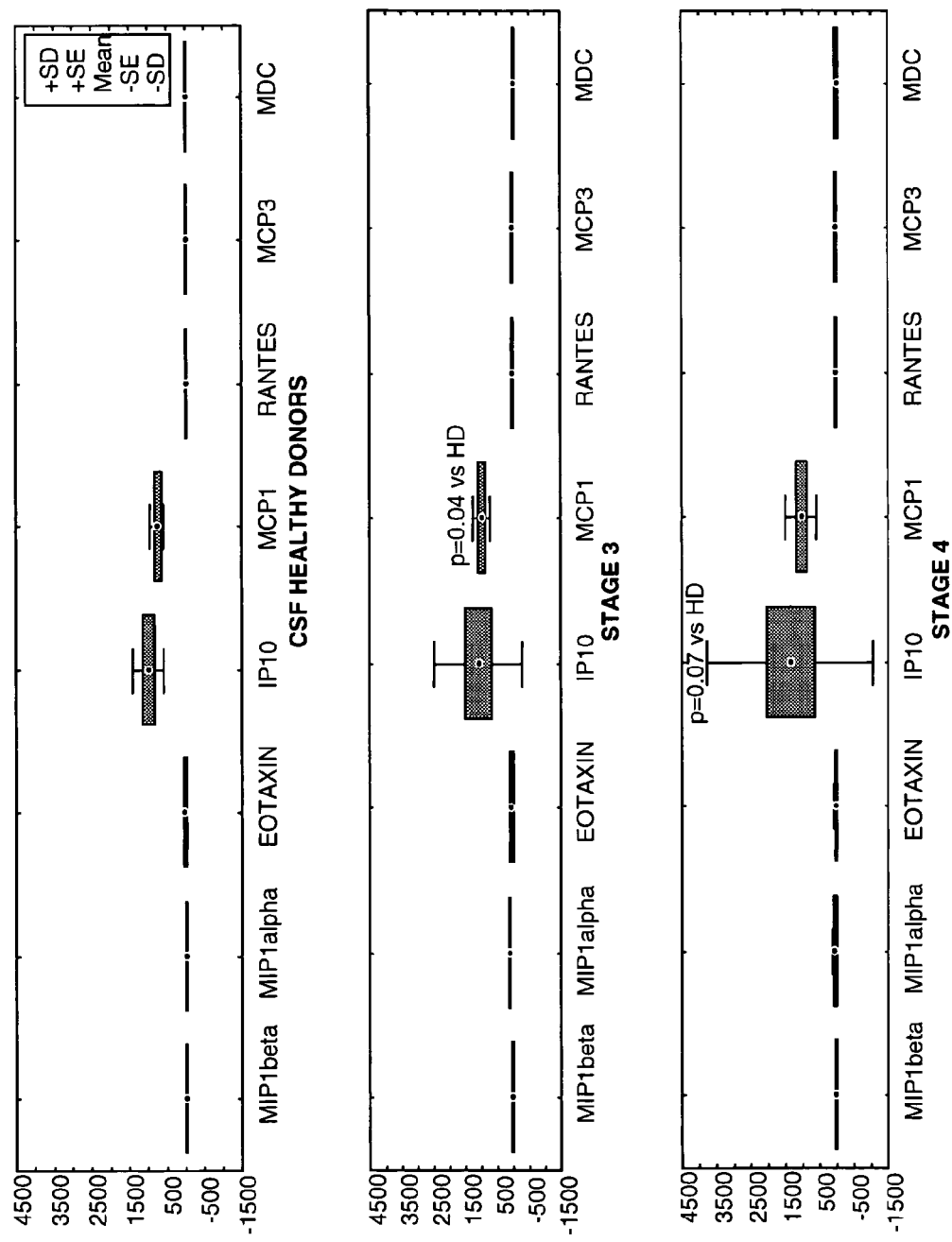
FIG. 5: Quantification of 24 cytokines and chemokines in CSF of stage 3 and stage 4 patients. A panel of 24 cytokines and chemokines have been quantified by MAP technology (Luminex) in CSF from HD, stage 3 and stage 4 patients. Box and Whisker Plots represent the mean±SD of a panel of chemokines. Only IP-10 and MCP-1 were detected at significant levels. p values are reported (non-parametric Mann-Whitney test) for statistical comparisons between patients and HD.
Figure 6:
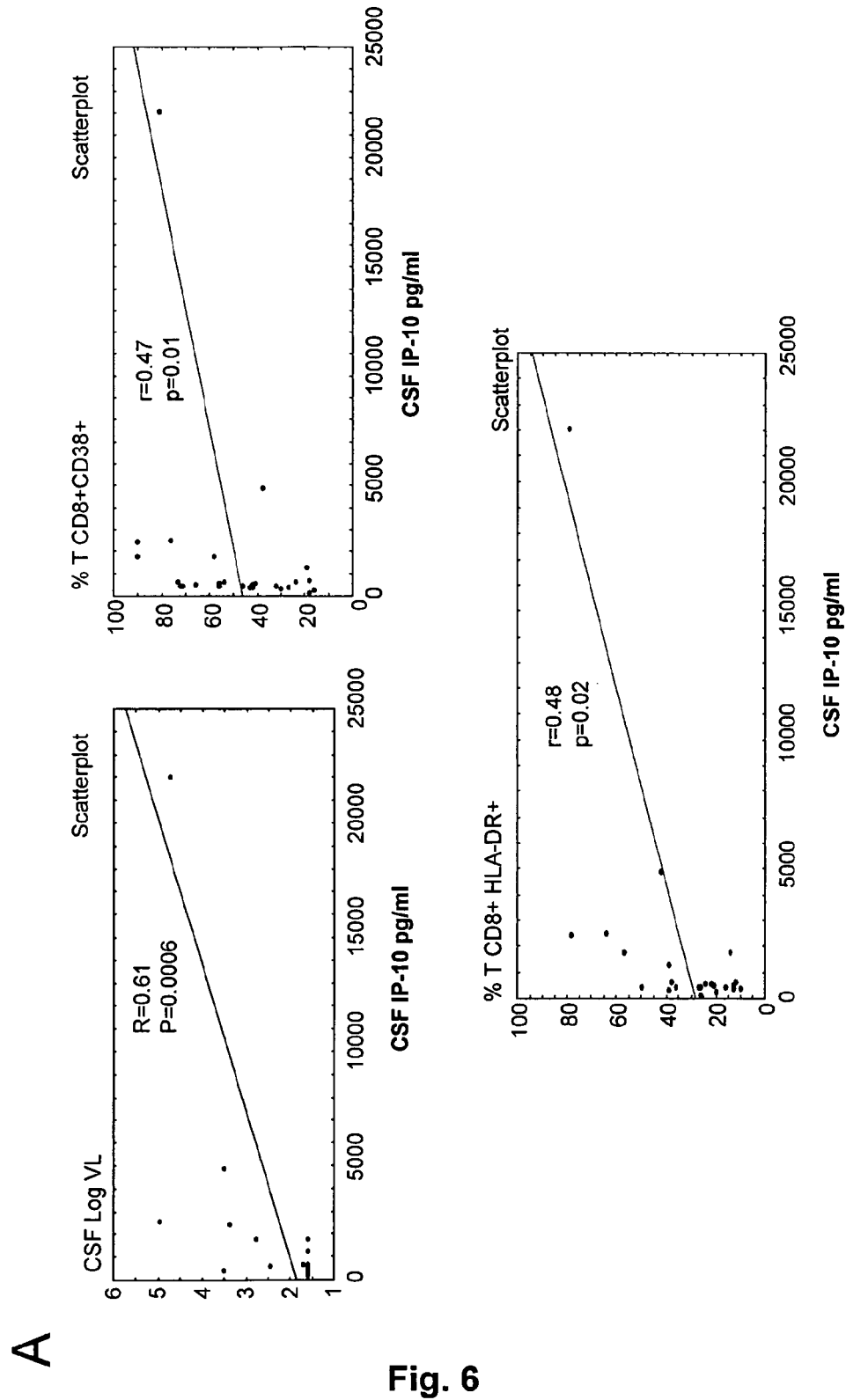
FIG. 6: Correlation of CSF IP-10 and MCP-1 levels with CSF viral load and disease evolution. A—Spearman correlations between CSF IP-10 and CSF VL, % T $CD8^+CD38^+$ and % $CD8^+$ $HLA-DR^+$. The coefficients of correlation (r) and p values are reported. B, C—Spearman correlations between CSF MCP-1 and the number of blood CD4 T cells, the % $CD8^+CD38^+$ T cells (B) and CSF IL-10 (C). The coefficients of correlation (r) and p values are reported.
Figure 6:
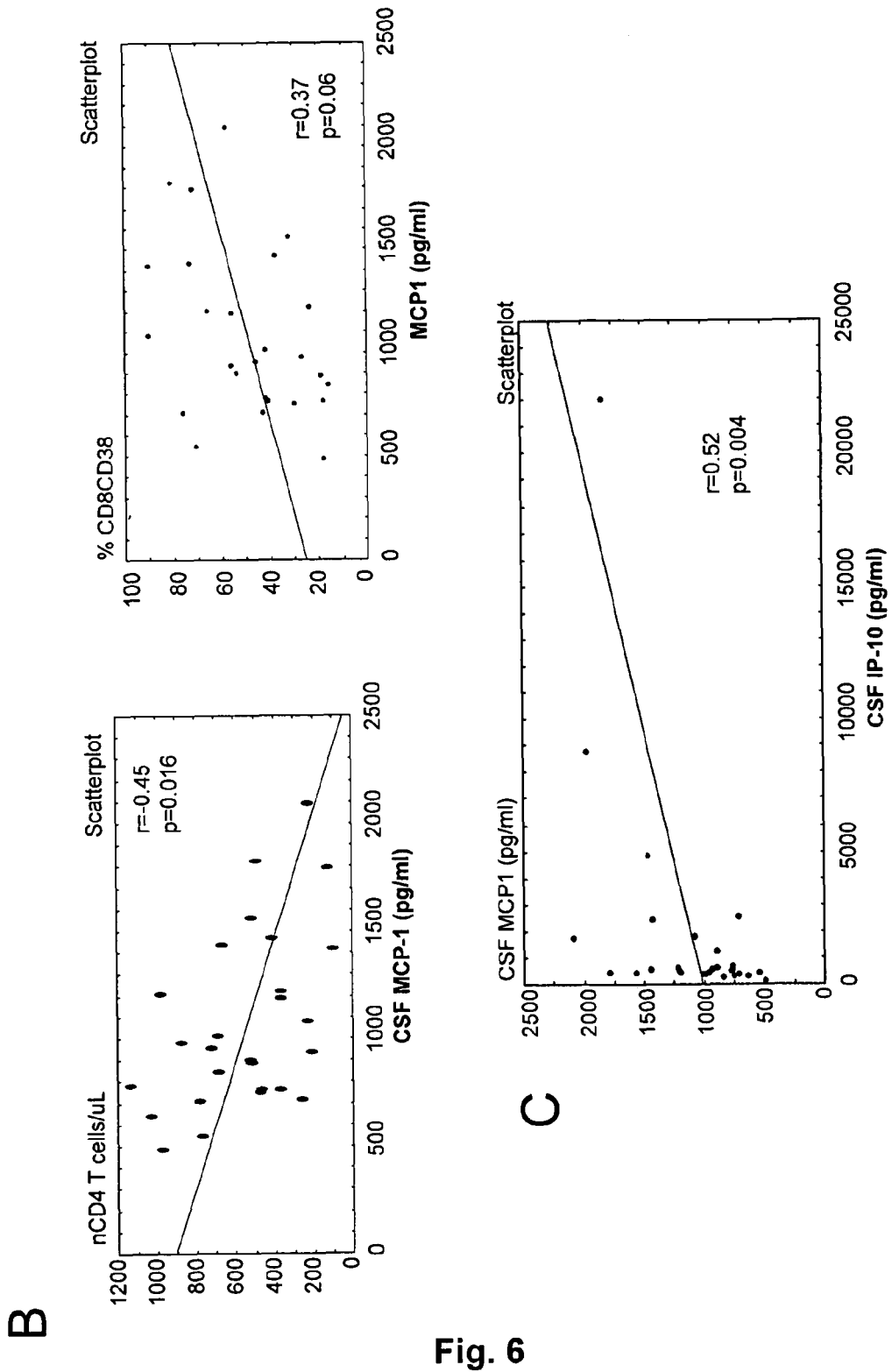

CSF from HD and HIV+ patients with neurological disorders at stage 3 or stage 4 were tested with the MAP (Multi-Analyte Profiling) technology for the simultaneous detection of 24 cytokine/chemokines. FIG. 5 shows the comparison of chemokine profiles in CSF from HD and HIV patients. In CSF from HD, cytokine/chemokine signatures were characterized by the detection of two chemokines, IP-10 and MCP-1. In CSF from HIV+ patients, these two chemokines were also detected, but at higher levels. Increased concentration of IP-10 in patients' CSF was correlated with CSF VL (in agreement with a previous report (Paola Cinquea et al. Cerebrospinal fluid interferon-γ-inducible protein 10 (IP-10, CXCL10) in HIV-1 infection. J Neuroimmunology 2005) and with the activation state of CD8 T cells (FIG. 6A). Similarly, increased concentrations of MCP-1 were correlated with the activation state of T cells, and MCP-1 levels appeared to be a correlate of disease evolution, as shown by the inverse correlation between CSF MCP1 concentration and CD4 T cell numbers (FIG. 6B). FIG. 6C shows that the levels of IP-10 and MCP-1 are positively correlated in patients' CSF.

Figure 7:
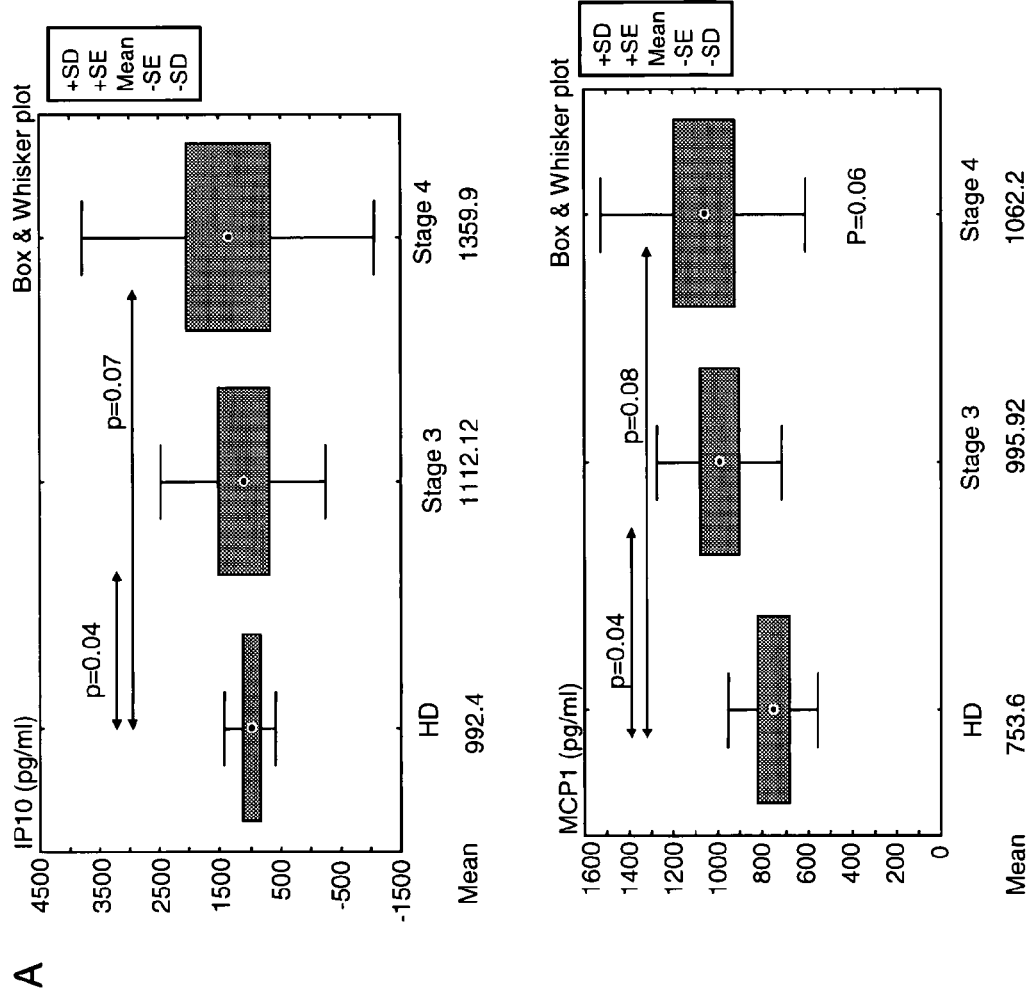
FIG. 7: Correlation of CSF IP-10 and MCP-1 in stage 3 and stage 4 patients, and with anti-HMGB1 antibodies. A—Comparative IP-10 (top panel) and MCP1 (bottom panel) concentrations in patients at stage 3 or stage 4 and HD. The mean values are indicated at the bottom of the figure. p values are reported (non-parametric Mann-Whitney test) for statistical comparisons between patients and HD. B—Spearman correlations between CSF anti-HMGB1 antibodies and CSF IP-10 or CSF MCP1 are shown. The coefficients of correlation (r) and p values are reported.
Figure 7:
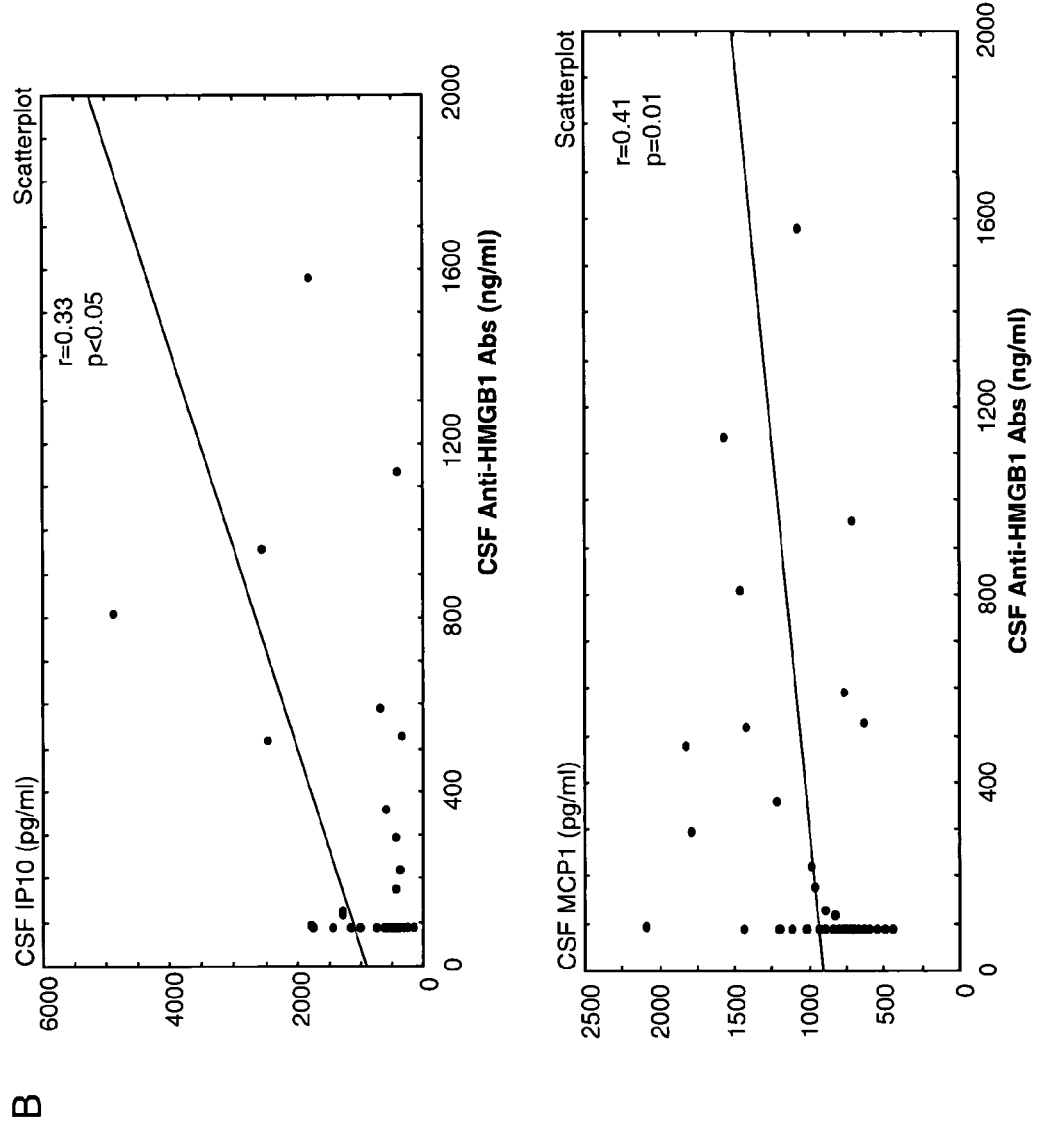

In order to characterize the nature of mediators detected in CSF from patients with neurological disorders, IP-10 and MCP-1 levels were compared between HD and stage 3 and stage 4 patients. FIG. 7A shows that stage 3 is associated with a significant increase of both IP-10 and MCP-1. Interestingly, CSF IP-10 and MCP-1 concentrations were positively associated with the levels of anti-HMGB1 antibodies (FIG. 7B).

Figure 8:
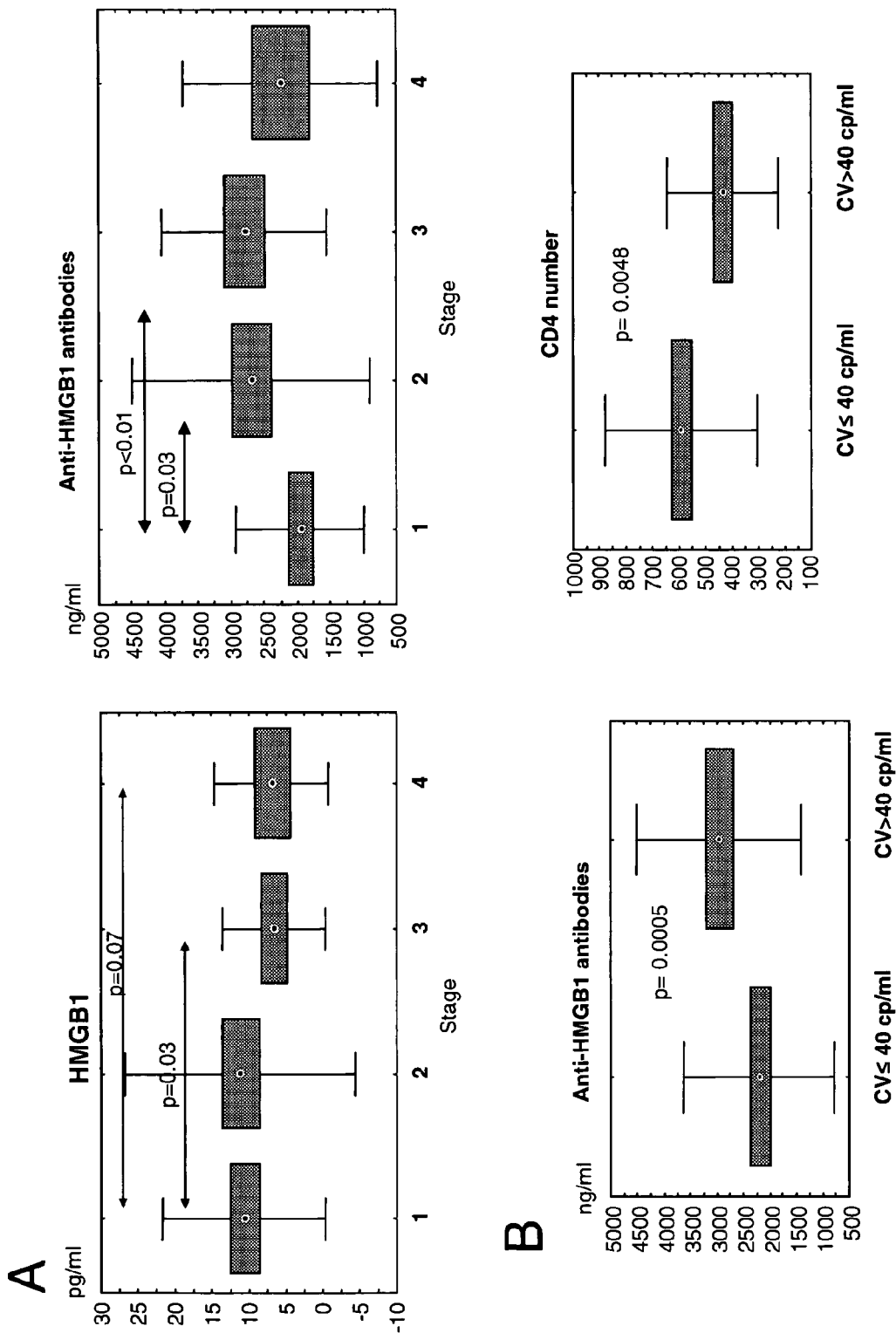
FIG. 8: Correlation of serum anti-HMGB1 antibody levels at stage 2 with plasma VL. A—Comparative serum HMGB1 (left panel) and anti-HMGB1 antibodies (right panel) concentrations in HIV-infected patients at stage 1 (n=33, no neurological disorder), stage 2 (n=41, mild neurological disorder), stage 3 (n=17) and stage 4 (n=13). p values are reported (non-parametric Mann-Whitney test) for statistical comparisons between the groups of patients. B—Patients were stratified into 2 groups according to CSF VL: undetectable (i.e. <40 cp/ml, n=55) and positive (VL<40 cp/ml, n=28). Anti-HMGB1 Abs and CD4 T cell numbers were compared between these 2 groups and p values are reported (non-parametric Mann-Whitney test). C—Patients were stratified according to VL as indicated on the x axis. Anti-HMGB1 antibodies and HMGB1 concentrations (top left and bottom panels) were compared for each group and p values are reported (non-parametric Mann-Whitney test). The top right panel shows the Spearman correlation between anti-HMGB1 antibodies and serum VL on 105 patients. The coefficients of correlation (r) and p values are reported.
Figure 8:
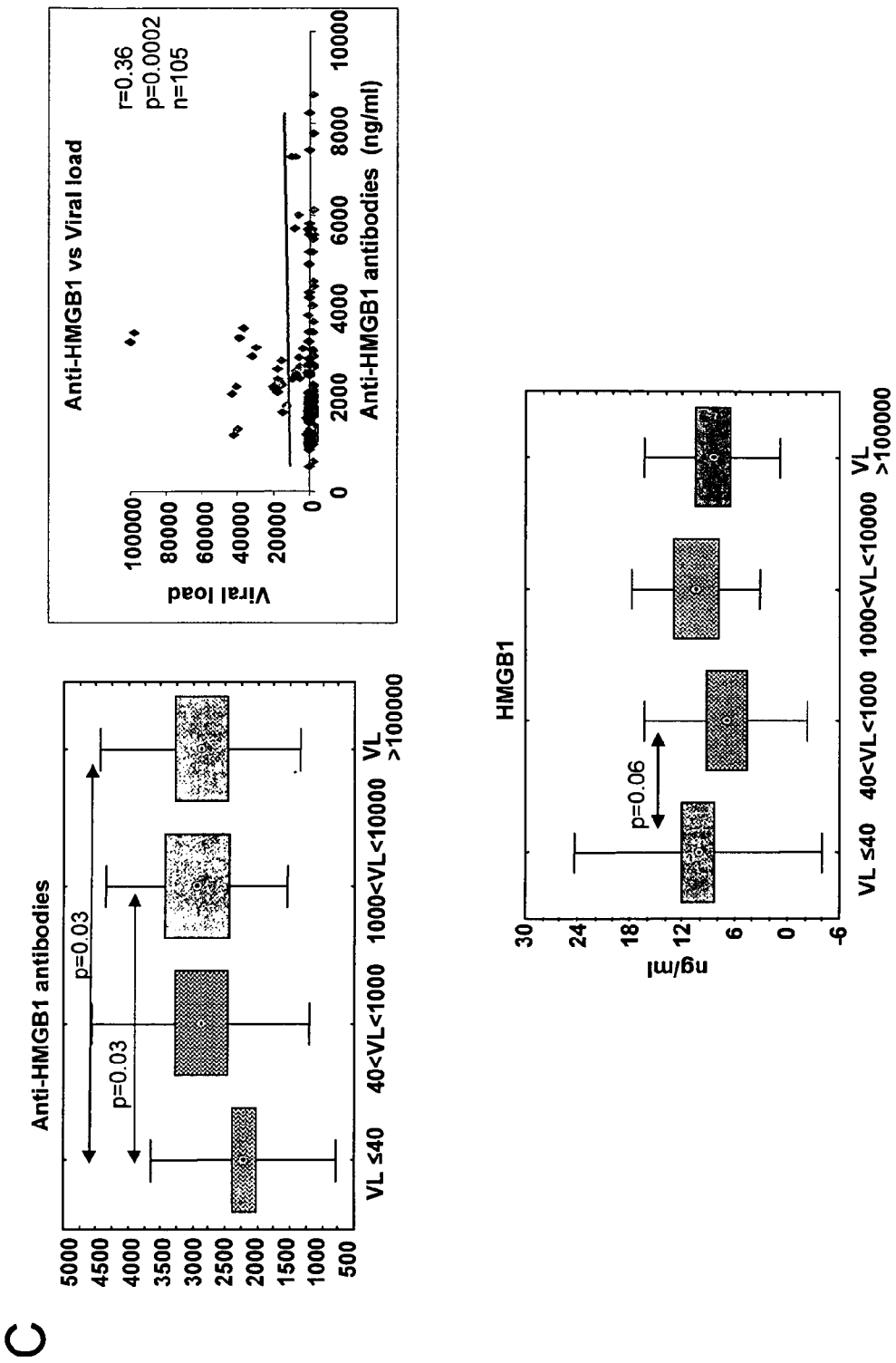

IIb. HMGB1, Anti-HMGB1 Antibodies and Chemokine Signatures in sera from HIV+ Patients with Neurological Disorders Serum Anti-HMGB1 Antibodies Levels are Increased from Stage 2 and Driven by HIV Viral Load FIG. 8A shows that, from stage 2, patients showed a significant increase in serum anti-HMGB1 antibody levels, whereas HMGB1 levels were less discriminating. There was no significant difference in VL between the different groups (not shown). Stratification of patients on the basis of serum viral load (undetectable <40 cp/ml vs positive >40 cp/ml) revealed that anti-HMGB1 antibodies were significantly increased in patients with detectable viral load (FIG. 8B). As expected, detectable VL was associated with reduced numbers of CD4 T cells (FIG. 8B). A more refined stratification of serum VL showed that anti-HMGB1 antibodies significantly rose from VL>1000 cp/ml, and HMGB1 Abs levels were positively correlated with VL (FIG. 8C). As observed in CSF, HMGB1 levels were less discriminating.

Serum Anti-HMGB1 Abs Levels are Correlated with IP-10 Concentrations

Figure 9:
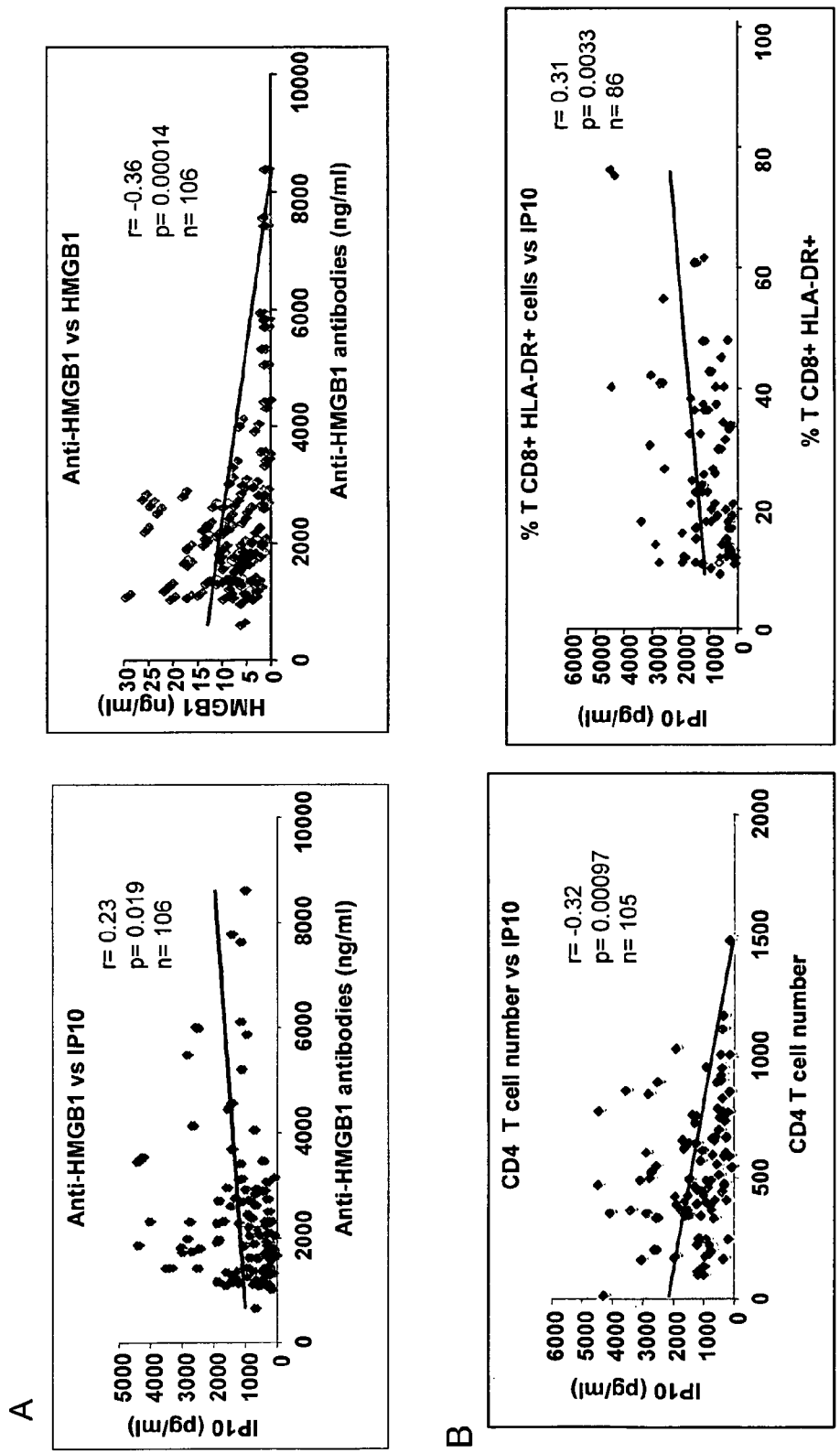
FIG. 9: Correlation between serum anti-HMGB1 antibody levels with IP-10 A—Spearman correlations between anti-HMGB1 antibody levels and IP-10 (left panel) or HMGB1 (right panel) on sera from 106 patients. The coefficients of correlation (r) and p values are reported. B—Spearman correlations between IP-10 and CD4 T cell number (left panel) or % T $CD8^+$ $HLA-DR^+$ (right panel) on sera from 105 and 86 patients respectively. The coefficients of correlation (r) and p values are reported.

As observed in patients' CSF, a positive correlation was found between anti-HMGB1 antibodies and IP-10 levels (FIG. 9A). IP-10 was found to be a correlate of disease evolution, since it increases with CD4 loss, and its production was associated to the persistent activation of the immune system, as evaluated by the expression of activation markers on T cells (FIG. 9B). Interestingly the levels of HMGB1 and anti-HMGB1 antibodies were inversely correlated (FIG. 9A) suggesting that the production of anti-HMGB1 antibodies is driven by the production of HMGB1, and that the anti-HMGB1 antibodies have a neutralizing activity.

IIc. Neurological Disorders in Patients with Suppressed Viral Load are Associated with Persistence of Anti-HMGB1 and Chemokines IP-10 and MCP-1 in CSF and Serum Suppression of Viral Load (VL) with HAART is Associated with Reduction of CSF Anti-HMGB1, HMGB1, IP-10, MCP-1 and Immune Activation.

Figure 10:
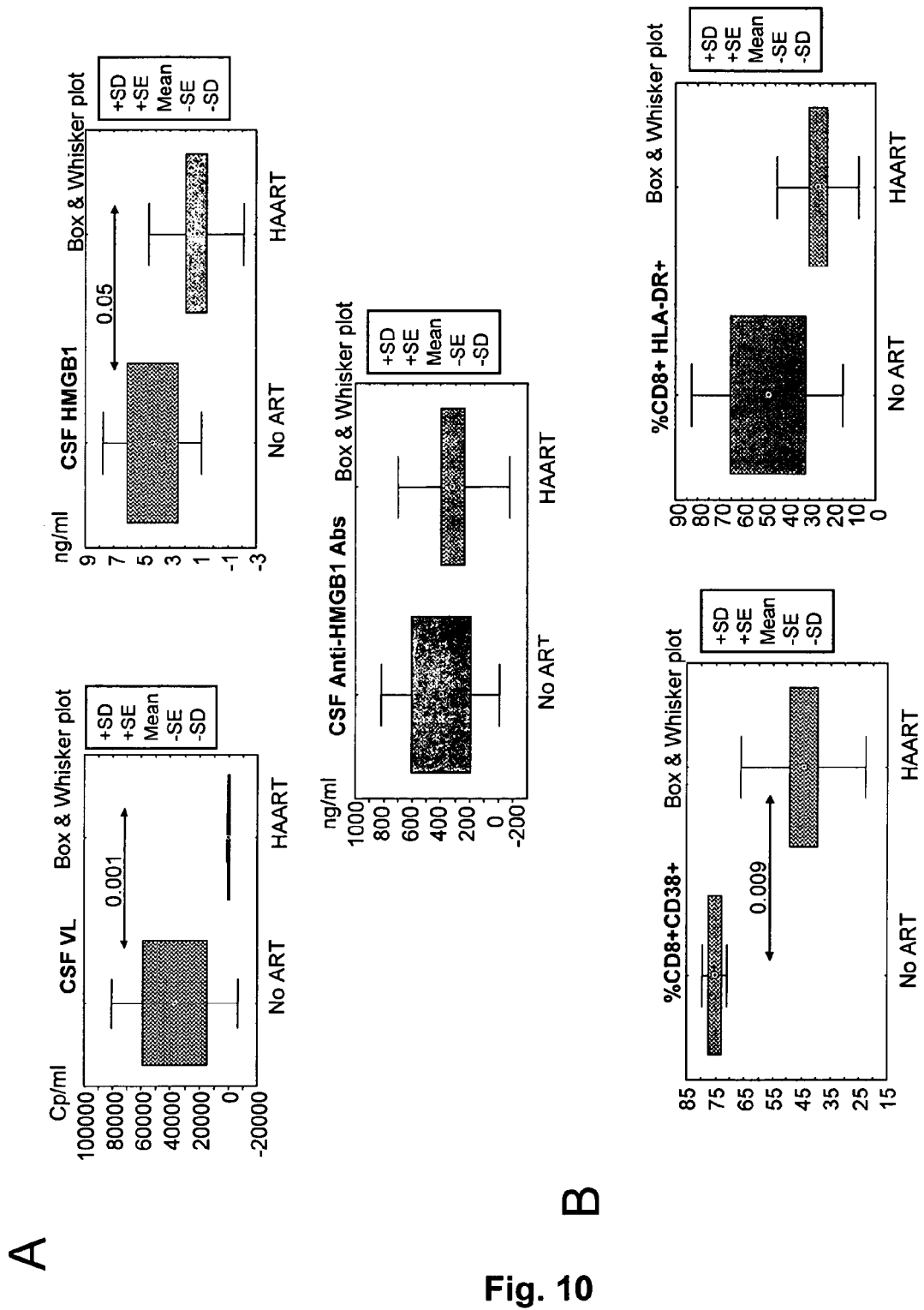
FIG. 10: Suppression of VL with HAART is associated with reduction of CSF anti-HMGB1, HMGB1, IP-10, MCP-1 and immune activation. Patients were stratified according to the fact that they received either HAART or no antiretroviral therapy. The mean levels of viral load (VL), HMGB1, anti-HMGB1 antibodies (Abs) (A), the percentage of CD8+ CD38+ and CD8+HLA-DR+ cells (B), and the levels of IP-10 and MCP1 (C) were compared between the two groups (non-parametric Mann-Whitney test). p values are reported.

Successful anti-retroviral therapy is associated with suppression of CSF viral load in most of the patients with neurological disorders (FIG. 10A). Concomitantly, the levels of CSF HMGB1, anti-HMGB1 (FIG. 10A), IP-10 and MCP1 (FIG. 10C) are reduced, and the expression of CD38 and HLA-DR on CD8 T cells as well (FIG. 10B).

Persistence of HMGB1, Anti-HMGB1, IP-10 and MCP1 in CSF from Patients with Suppressed Viral Load Compared to Healthy Donors.

Figure 11:
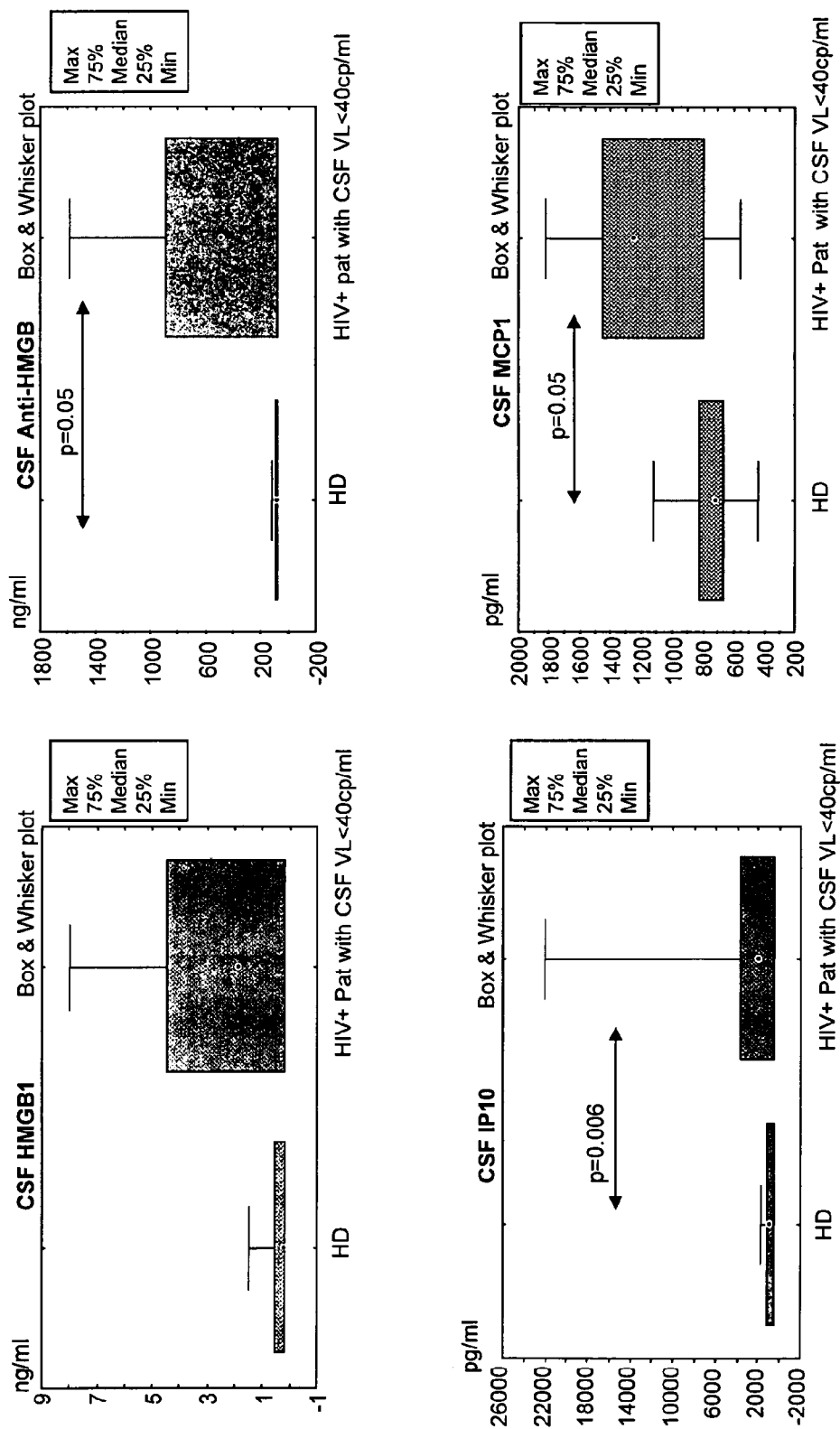
FIG. 11: Persistence of HMGB1, anti-HMGB1, IP-10 and MCP1 in CSF from patients with suppressed viral load. HMGB1, anti-HMGB1, IP-10 and MCP1 levels were compared in CSF in 66 patients with VL<40 cp/ml and 10 healthy donors (HD). The median values (25%-75% percentiles) are shown. Statistical comparisons were made with the non-parametric Mann-Whitney test. p values are reported.

Comparison of cytokine/chemokine levels in CSF from HIV+ patients with VL<40 cp/ml and in CSF from healthy donors revealed the persistence of HMGB1, anti-HMGB1, IP-10 and MCP-1 (FIG. 11). Thus these data show that neurological disorders that persist despite VL suppression are associated with elevated levels of anti-HMGB1, IP-10 and MCP1 molecules in CSF.

Serum Anti-HMGB1 Abs Distinguish Patients with Stages 2 to 4 from Stage 1 Patients, in Spite of Suppression of Viral Replication.

Figure 12:
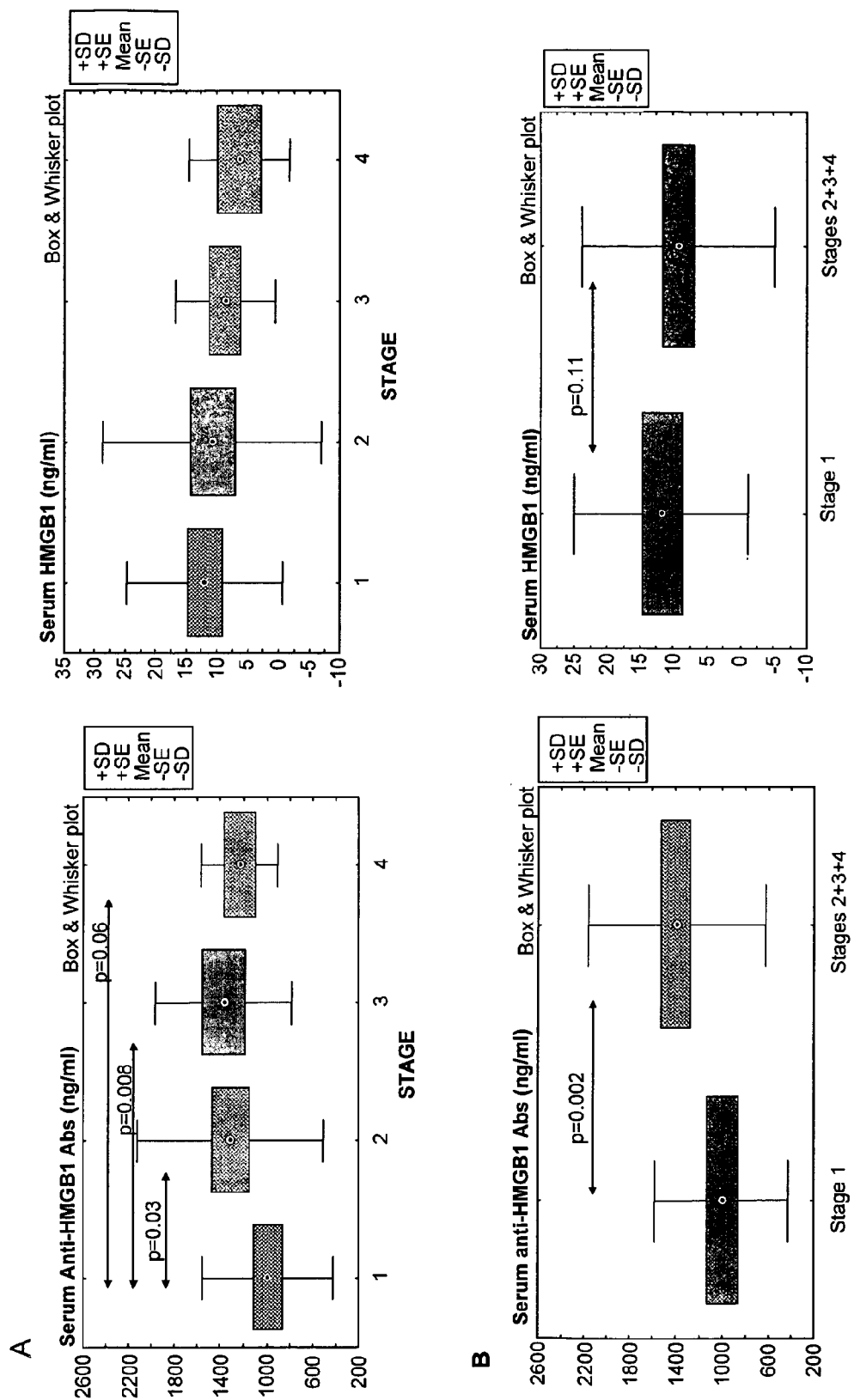
FIG. 12: Neurological disorders are associated with increased levels of serum anti-HMGB1 Abs in patients with suppressed VL. The levels of anti-HMGB1 antibodies (Abs) and HMGB1 were compared between the different neurological stages (A) or between patients with stages 2, 3 and 4 (n=45) and stage 1 patients (n=21) (B), all of them presenting with a VL<40 cp/ml. Mean values are shown and statistical comparisons were made with the non-parametric Mann-Whitney test. p values are reported.
Figure 12:
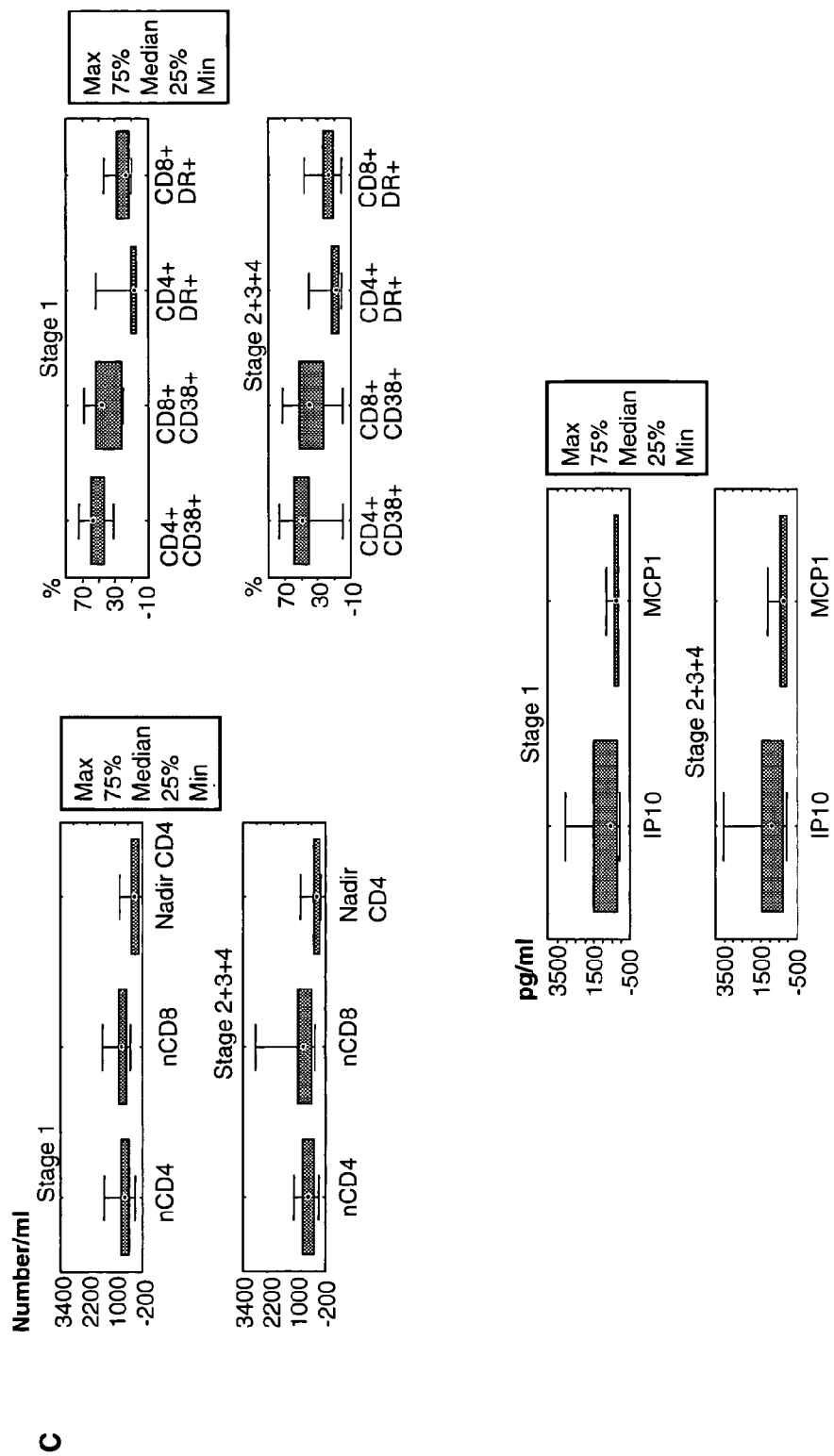

Anti-HMGB1 Abs were found still significantly increased in HIV+ patients with stages 2 to 4 compared to HIV+ patients at stage 1 (with no neurological troubles), although all these patients showed undetectable levels of VL (<40 cp/ml) (FIG. 12A). FIGS. 12B and 12C show that neither HMGB1, IP-10 or MCP-1 levels, nor the nCD4 T cells, nCD8 T cells, Nadir CD4, the percentages of activated CD4 and CD8 T cells, was found different in patients with stages 2, 3 and 4 versus patients with stage 1. Therefore, anti-HMGB1 levels represent the only factor that distinguishes patients with stages 2, 3 and 4 from those with stage 1.

Correlations Between Anti-HMGB1, MCP1, IP-10 and Immune Activation in Patients with Stages 2, 3 and 4 and Suppressed Viral Load To understand the causes of persistent anti-HMGB1 levels despite controlled viral load, Spearman correlations were analyzed between various parameters associated with clinical evolution. FIG. 13A shows that anti-HMGB1 levels are positively correlated with IP-10 and MCP-1 levels, being themselves related to the state of immune activation, measured by the expression of HLA-DR and CD38 on CD4 and CD8 T cells (FIG. 13B). As already observed in the whole cohort (discussed above), the state of immune activation is a correlate of disease evolution measured by the number of CD4 T cells (FIG. 13C). Overall, these data show that a persistent immune activation is detected in patients with suppressed viral load and stages 2, 3 and 4, driving the production of anti-HMGB1 Abs. The negative correlation between serum anti-HMGB1 and HMGB1 found both in the whole cohort of patients (stage 1 to stage 4 with variable viral load) (FIG. 9A) and in patients with stages 2, 3 and 4 and suppressed viral load (FIG. 13A) suggest an in vivo neutralizing activity of the antibodies.

The study of the immunological parameters characterizing a cohort of patients was pursued with two aims:
(1) to extend the analysis to the sera of the whole cohort (n=106 patients) in order both to determine if the molecular signature reported in CSF with classification stages 3 and 4 was also found in serum of patients and with the HAND/no HAND classification; and
(2) to assess whether Magnetic Resonance Imaging (MRI) measurements that identify basal ganglia volumetric changes, and metabolic changes linked to CNS alterations, were correlated with this molecular signature.

III. Level of Circulating HMGB1 Protein and Level of Total Anti-HMGB1 Antibodies are the only Parameters that Distinguish HAND Patients from No HAND Patients To define HAND, the criteria put forward by Antinori et al. (Neurology. 2007 Oct. 30; 69(18):1789-99) were used. The following correspondence with the classification stage 1 to stage 4 described above was considered: no HAND (stages 1 and 2); HAND (stages 3 and 4).

FIG. 14 shows the clinical and immunological parameters that characterize the cohort of patients studied. The majority of these patients (81%) received potent antiretroviral therapy, and 67% had a suppressed viral load. Immune deficiency, as measured by CD4 counts, was moderate, and nadir CD4 counts (i.e., the lowest CD4 value reached since the beginning of the infection) were not low. The degree of immune activation was moderate, considering that in an untreated patient at the AIDS stage, 60 to 100% of $CD8^+$ T cells coexpress the activation markers CD38 and HLA-DR.

One third of these patients had HAND (see below for detailed information), and comparison with the no HAND groups showed no difference regarding the viral load, the CD4 and nadir CD4 counts, the proportion of viremic patients and the level of immune activation.

Strikingly, the only significant difference between these two groups was detected for HMGB1 and anti-HMGB1 antibodies (p=0.006, and p=0.05 respectively, non parametric Mann-Witney test). IP-10 and MCP-1 serum levels could not discriminate between HAND and no HAND patients (FIG. 14). Similarity of immunological and virological parameters, in HAND and no HAND patients, is shown as histograms in FIG. 15.

As mentioned above, HMGB1 and anti-HMGB1 were the only two parameters discriminating the two groups of patients (FIG. 16). This discrimination was independent of RNA viral load, since it was also observed in aviremic patients (VL<40 copies/ml).

Although the levels of IP-10 and MCP1 chemokines were not statistically different between HAND and no HAND patients (FIG. 14), their production during the infection was found positively correlated with persistent immune activation, the levels of anti-HMGB1 and MCP-1 and disease evolution, suggesting that chronic inflammation was responsible for chemokines release (FIGS. 17 and 18). These observations confirm the conclusions previously reported for the CSF of HIV-infected patients (example IIA and FIGS. 5, 6 and 7).

IV. An Immunological Signature Correlated to Volumetric and Metabolic Changes in Basal Ganglia in HIV-Infected Patients with HAND Each patient performed neurological tests exploring a wide spectrum of cognitive domains. According to the NP test results, patients were divided in two groups, those with HAND or without HAND (see Antinori et al. above). MRI analysis was performed for some patients. An average 3D image was created, and was further fused with a digital brain atlas (from the Montreal Neurological Institute), wherein left and right basal ganglia (BG) had been identified. This enabled for each image to calculate the volume and the amount of dilatation or shrinkage, measured by the Jacobian value. Values lower than 1 indicate a dilatation of the subject image with respect to the template, while values above 1 suggest volume reduction. Metabolic changes in BG were calculated. Choline/N-acetyl Aspartate (Cho/NAA) is a marker of neuronal inflammation and was determined as previously described in the literature (Ratai E M et al. PLoS One. 2010 May 7; 5(5):e10523; Yiannoutsos C T et al. Neuroimage. 2008 Mar. 1; 40(1):248-55. Paul R H et al. J Neuropsychiatry Clin Neurosci. 2007 Summer;19(3):283-92 Greco J B et al. Magn Reson Med. 2004 June;51(6):1108-14. Meyerhoff D J et al. AJNR Am J Neuroradiol. 1996 May;17(5):973-8). In the BG of cognitively impaired HIV-infected patients, the Cho/NAA ratio is generally increased.

FIG. 19A shows that patients with HAND had larger putamen (Jacobian value lower than 1; p=0.008). Patients with HAND had higher Cho/NAA ratios on MRI-spectroscopy of BG (FIG. 19B). Relationships between volumetric and metabolic parameters are shown in FIG. 19C: larger volumes of putamen were correlated to Cho/NAA values above 0.575 (p=0.02).

To investigate a possible relationship between neurological and immunologic parameters, patients were stratified according to Cho/NAA ratios, and immune markers were compared. FIG. 20 shows that an increased immune activation (% of CD8$^+$CD38$^+$HLA-DR$^+$ T cells) and high levels of anti-HMGB1 and IP10 correlate to increased Cho/NAA values.

CONCLUSION

This detailed analysis of soluble mediators detected in serum and CSF from HIV-infected patients, some of them suffering from AIDS-associated neurological disorders, showed in CSF a profile of inflammation, characterized by important levels of anti-HMGB1 antibodies (in reaction to released HMGB1) associated with high expression of the chemokine IP-10. Chemokines have been implicated in the immunopathogenesis of neurological disorders, such as Multiple Sclerosis (MS), and in particular IP-10 was reported to be increased in CSF from MS patients when inflammation is prominent (Scarpini E et al. J Neurological Sciences 195:41, 2002). In HIV-infected patients, a study reported that IP-10 levels were increased in subjects with primary and asymptomatic HIV infections and AIDS dementia complex, and positively correlated with CSF viral load (Paola Cinquea et al. Cerebrospinal fluid interferon-γ-inducible protein 10 (IP-10, CXCL10) in HIV-1 infection. J Neuroimmunology 2005). IP-10 is a potent chemoattractant and it has been suggested to enhance retrovirus infection and mediate neuronal injury. The proinflammatory properties of MCP1 and its ability to up-regulate HIV-1 replication was also suggested to contribute to the development of increased risk of dementia. MCP-1 may facilitate migration of infected and/or activated monocytes into the brain where they become host cells for HIV-1 replication and by activating macrophages, microglia and astrocytes that results in release of a number of potent neurotoxins (Dhillon et al. Roles of MCP-1 in development of HIV-dementia. Front Biosci. 2008, 13: 3913-3918). Our observations bring new findings demonstrating that the alarmin HMGB1, and most importantly the antibodies specific for this alarmin, are detected (in addition to IP-10 and MCP-1) in CSF from HIV-infected patients with stages 2 to 4, and that they represent a correlate of viral replication and disease evolution. Moreover, the persistence of anti-HMGB1 antibodies in patients with suppressed viral replication is a determinant of stages 2 to 4.

The results on the no HAND/HAND cohort show that HAND is associated with an inflammatory pattern that can be revealed with MRI (larger putamen, increased Cho/NAA) and/or through immune markers, including activation markers on peripheral T cells (CD38 and HLA-DR expression) and/or inflammatory mediators. This study shows for the first time that total serum anti-HMGB1 antibodies and IP-10 levels are correlated with BG alterations in patients with HAND, confirming the importance of measuring these two molecules in the blood of patients developing HAND. Importantly, these observations link for the first time MRI and spectroscopy parameters associated with HAND, such as larger putamen and increased Cho/NAA levels, with immunological parameters (anti-HMGB1 antibodies and IP10) and immune activation/inflammation markers.

These results suggest that the combination of HMGB1/ anti-HMGB1 antibodies, IP-10, MCP-1, is both a response to and contributing determinant of local infection in CNS. This application shows that the molecular signature anti-HMGB1 antibodies and IP-10 and/or MCP-1 may be useful in the diagnosis and prognosis of diseases in which HMGB1 has been shown to be involved, with or without neurological disorders, such as AIDS.

Modifications and Other Embodiments

Various modifications and variations of the disclosed products, compositions, and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, immunological, biological, chemical or pharmacological arts or related fields are intended to be within the scope of the following claims.

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

The invention claimed is:

1. A method for quantitating the antibodies specific for High Mobility Group Box I (HMGB1) in a sample obtained from a patient comprising:
   a) contacting a cerebrospinal fluid sample, or both a sample of serum and a sample of cerebrospinal fluid, obtained from said patient with native HMGB1 protein or derivatives thereof; and
   b) quantitating the antibodies specific for High Mobility Group Box I (HMGB1) contained in said cerebrospinal fluid sample, or said both sample of serum and sample of cerebrospinal fluid.

2. The method of claim 1, wherein the patient is infected with HIV.

3. The method of claim 2, wherein the higher the level of antibodies specific for HMGB1, the higher the state of progression towards neurological disorders associated with HIV infection.

4. The method of claim 2, wherein the higher the level of antibodies specific for HMGB1, the higher the immune deficiency of the patient.

5. The method of claim 2, wherein the more persistent the level of antibodies specific for HMGB1, the higher the immune activation of the patient.

6. The method of claim 1, wherein the level of antibodies specific for HMGB1 correlates the diagnosis of the presence of neurological disorders by conventional clinical criteria.

7. The method of claim 1, further comprising quantitating the chemokine IP-10 and/or the chemokine MCP-1 in said sample.

8. The method of claim 7, wherein the higher the level of antibodies specific for HMGB1 and the higher the level of chemokine IP-10 and/or the higher the level of chemokine MCP-1, higher the state of progression towards neurological disorders associated with AIDS.

9. The method of claim 1, wherein the patient has a neurological disorders associated with a disease or disorder selected from the group consisting of diseases or disorders of infectious origin, bacterial infection, pathogen infection, viral infection, or infection by prion.

10. The method of claim 1, wherein the patient has a neurological disorders associated with a disease or disorder, the origin of which is non-infectious or the origin of which is unknown.

11. The method of claim 1, further comprising:
    (a) identifying volumetric changes in the basal ganglia of said patient by Magnetic Resonance Imagining measurements; and/or
    (b) identifying metabolic changes in the basal ganglia of said patient by calculating the serum Choline/N-acetyl Aspartate ratio (Cho/NAA).

12. The method of claim 1, wherein said patient is infected by HIV and is under retroviral therapy.

13. The method of claim 3, wherein said patient is under retroviral therapy.

14. An in vitro method for monitoring the condition of a subject who is known to be infected with HIV, comprising:
    a) quantitating the antibodies specific for High Mobility Group Box I (HMGB1) contained in a cerebrospinal fluid sample, or both a sample of serum and a sample of cerebrospinal fluid, by contacting said sample(s) obtained from said subject with native HMGB1 protein or derivatives thereof; and
    b) quantitating the chemokine IP-10 and/or the chemokine MCP-1 in said same sample(s) obtained from said subject.

15. The method according to claim 14, wherein said quantitated HMGB1, and said quantitated IP-10 and/or said quantitated MCP-1 are compared respectively to the amount of quantitated HMGB1, and quantitated IP-10 and/or quantitated MCP-1 from a sample obtained from a subject not infected with HIV, or from a sample obtained from the same subject at a different time or at different times.

16. The method according to claim 1, comprising:
    a) contacting a cerebrospinal fluid sample with native HMGB1 protein or derivatives thereof; and
    b) quantitating the antibodies specific for HMGB1 in the cerebrospinal fluid sample.

17. The method according to claim 1, comprising before contacting the sample with native HMGB1 protein or derivatives thereof, a step of treating the sample by an acid treatment to dissociate the immune complexes in the sample, and wherein in said method, the quantitated antibodies specific for High Mobility Group Box I (HMGB1) are total antibodies specific for HMGB1.

18. The method according to claim 17, wherein the immune complexes in the sample are dissociated with Glycine 1.5M at a low pH.

19. The method according to claim 14, comprising before contacting the sample with native HMGB1 protein or derivatives thereof, a step of treating the sample by an acid treatment to dissociate the immune complexes in the sample, and wherein in said method, the quantitated antibodies specific for High Mobility Group Box I (HMGB1) are total antibodies specific for HMGB1.

20. The method according to claim 19, wherein the immune complexes in the sample are dissociated with Glycine 1.5M at a low pH.

21. The method according to claim 16, comprising before contacting the sample with native HMGB1 protein or derivatives thereof, a step of treating the sample by an acid treatment to dissociate the immune complexes in the sample, and wherein in said method, the quantitated antibodies specific for High Mobility Group Box I (HMGB1) are total antibodies specific for HMGB1.

22. The method according to claim 1, wherein the immune complexes found in the sample are dissociated with Glycine 1.5M at a low pH.

23. An in vitro method for monitoring HIV infection in a subject infected with HIV comprising quantitating High Mobility Group Box I (HMGB1) protein contained in a cerebrospinal fluid sample obtained from said subject, wherein said HMGB1 protein targeted for quantitation is either total HMGB1 or its circulating fraction (circulating HMGB1) or its immunologically complexed fraction.

24. The method according to claim 23, wherein said quantitated HMGB1 is compared to the amount of HMGB1 from a cerebrospinal fluid sample obtained from a subject not infected with HIV or to the amount of HMGB1 from a cerebrospinal fluid sample obtained from the same subject at a different time.

25. An in vitro method for quantitating the antibodies specific for High Mobility Group Box I (HMGB1) contained in a cerebrospinal fluid sample obtained from a subject, comprising:
    a) contacting said cerebrospinal fluid sample with native HMGB1 protein or derivatives thereof; and
    b) quantitating the antibodies specific for HMGB1.

* * * * *